(12) United States Patent
Kusters et al.

(10) Patent No.: US 12,247,912 B2
(45) Date of Patent: Mar. 11, 2025

(54) AUTOMATED ADJUSTMENT OF THE POSITION OF THE LIGHT SOURCE OF A DETECTION ASSEMBLY FOR INCREASED LIGHT RECEPTION

(71) Applicant: Fenwal, Inc., Lake Zurich, IL (US)

(72) Inventors: Benjamin E. Kusters, Pleasant Prairie, WI (US); Ryan Murphey, Burlington, WI (US)

(73) Assignee: Fenwal, Inc., Lake Zurich, IL (US)

( * ) Notice: Subject to any disclaimer, the term of this patent is extended or adjusted under 35 U.S.C. 154(b) by 525 days.

(21) Appl. No.: 17/487,092

(22) Filed: Sep. 28, 2021

(65) Prior Publication Data

US 2022/0099562 A1    Mar. 31, 2022

Related U.S. Application Data

(60) Provisional application No. 63/085,293, filed on Sep. 30, 2020.

(51) Int. Cl.
*G01N 21/07* (2006.01)
*A61M 1/36* (2006.01)
(Continued)

(52) U.S. Cl.
CPC .......... *G01N 21/07* (2013.01); *A61M 1/3622* (2022.05); *A61M 1/3693* (2013.01); *H02P 8/14* (2013.01);
(Continued)

(58) Field of Classification Search
CPC ... G01N 21/07; G01N 33/491; A61M 1/3622; A61M 1/029; A61M 2205/3306; A61M 1/3693; H02P 8/14; B04B 2013/006
See application file for complete search history.

(56) References Cited

U.S. PATENT DOCUMENTS 5,194,145 A    3/1993   Schoendorfer
5,316,667 A    5/1994   Brown et al.
(Continued)

FOREIGN PATENT DOCUMENTS

WO    WO 2018/053217 A1    3/2018
WO    WO 2020/006549 A1    1/2020

OTHER PUBLICATIONS

European Patent Office, "Extended European Search Report", issued in connection with European patent application No. 21199 306.8 on Feb. 14, 2022, 8 pages.

*Primary Examiner* — Michael P LaPage
(74) *Attorney, Agent, or Firm* — Cook Alex Ltd.

(57) ABSTRACT

A fluid processing device includes a detection assembly having a light source, an adjustment system, and a light detector. The light source is associated with a component of the fluid processing device, provided in an initial position with respect to said component of the fluid processing device, and configured to emit a light. The adjustment system is associated with the light source and configured to adjust the position of the light source. The light detector is configured to receive at least a portion of the light from the light source and generate a signal indicative of the amount of light received by the light detector. The fluid processing device further includes a controller configured to receive the signal from the light detector and control the adjustment system to move the light source to a monitoring position based at least in part on the signal.

18 Claims, 20 Drawing Sheets

(51) Int. Cl.
*H02P 8/14* (2006.01)
*B04B 13/00* (2006.01)
*G01N 33/49* (2006.01)

(52) U.S. Cl.
CPC ............... *A61M 2205/3306* (2013.01); *B04B 2013/006* (2013.01); *G01N 33/491* (2013.01)

(56) References Cited

U.S. PATENT DOCUMENTS

| | | | |
|---|---|---|---|
| 5,632,893 | A | 5/1997 | Brown et al. |
| 5,868,696 | A | 2/1999 | Giesler et al. |
| 6,002,474 | A * | 12/1999 | Thomas ............... G01N 15/042 |
| | | | 356/244 |
| 8,075,468 | B2 | 12/2011 | Min et al. |
| 2005/0051466 | A1 | 3/2005 | Carter et al. |
| 2006/0001860 | A1* | 1/2006 | Scibona ................ G01N 15/05 |
| | | | 356/39 |
| 2008/0283781 | A1* | 11/2008 | Carter .................... G01N 15/05 |
| | | | 250/573 |
| 2009/0156383 | A1* | 6/2009 | Ladtkow .............. G01N 33/491 |
| | | | 494/10 |
| 2009/0246082 | A1* | 10/2009 | Saiki ....................... G01N 21/07 |
| | | | 422/72 |
| 2015/0219558 | A1* | 8/2015 | Koudelka ............... B04B 13/00 |
| | | | 356/39 |
| 2017/0319809 | A1* | 11/2017 | Biba .................... A61M 16/107 |
| 2019/0201916 | A1* | 7/2019 | Min ...................... A61M 1/3603 |
| 2020/0072729 | A1 | 3/2020 | Lumpkin et al. |

\* cited by examiner

AUTOMATED ADJUSTMENT OF THE POSITION OF THE LIGHT SOURCE OF A DETECTION ASSEMBLY FOR INCREASED LIGHT RECEPTION

CROSS-REFERENCE TO RELATED APPLICATIONS

This application claims the benefit of and priority of U.S. Provisional Patent Application Ser. No. 63/085,293, filed Sep. 30, 2020, the contents of which are incorporated by reference herein.

BACKGROUND

Field of the Disclosure

The present disclosure relates to detection assemblies. More particularly, the present disclosure relates to adjustment of the position of the light source of a detection assembly.

Description of Related Art

Various blood processing systems now make it possible to collect particular blood constituents, rather than whole blood, from a blood source. Typically, in such systems, whole blood is drawn from a source, the particular blood component or constituent is removed and collected, and the remaining blood constituents are returned to the source.

Whole blood is typically separated into its constituents through centrifugation. This requires that the whole blood be passed through a centrifuge after it is withdrawn from, and before it is returned to, the source. To avoid contamination and possible infection of the source, the blood is preferably contained within a sealed, sterile fluid flow circuit during the entire centrifugation process. Typical blood processing systems thus include a permanent, reusable centrifuge assembly containing the hardware (drive system, pumps, valve actuators, programmable controller, and the like) that spins and pumps the blood, and a disposable, sealed and sterile fluid processing assembly that is mounted in cooperation on the hardware. The centrifuge assembly engages and spins a disposable centrifuge chamber of the fluid processing assembly during a collection procedure. The blood, however, makes actual contact only with the fluid processing assembly, which assembly is used only once and then discarded.

As the whole blood is spun by the centrifuge, the heavier (greater specific gravity) components, such as red blood cells, move radially outwardly away from the center of rotation toward the outer or "high-G" wall of the separation chamber. The lighter (lower specific gravity) components, such as plasma, migrate toward the inner or "low-G" wall of the separation chamber. Various ones of these components can be selectively removed from the whole blood by forming appropriately located channeling seals and outlet ports in the separation chamber.

It is known to employ an optical sensor assembly to monitor the flow of blood and/or blood components through the flow circuit in the centrifuge and determine various characteristics of the flow. For example, PCT Patent Application Publication No. WO 2018/053217 A1 (which is hereby incorporated herein by reference) relates to an optical sensor assembly for viewing into the centrifuge chamber for detecting and controlling the location of an interface between separated blood components. In this assembly, as in any other detection assembly, proper alignment of the various components of the detection assembly with respect to the subject being monitored is necessary to ensure that fluid is being properly monitored during a procedure. It may be the case that the fluid flow circuit is mounted to the hardware in a way that affects the performance of the detection assembly, such that it would be advantageous to enable adjustment of the light source of the detection assembly in response to the orientation of a disposable circuit mounted to the hardware (or in response to some other factor) for improved performance.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a fluid processing device includes a detection assembly having a light source, an adjustment system, and a light detector. The light source is associated with a component of the fluid processing device, provided in an initial position with respect to said component of the fluid processing device, and configured to emit a light. The adjustment system is associated with the light source and configured to adjust the position of the light source with respect to the associated component of the fluid processing device. The light detector is configured to receive at least a portion of the light from the light source and generate a signal indicative of the amount of light received by the light detector. The fluid processing device also includes a controller configured to receive the signal from the light detector and control the adjustment system to move the light source with respect to the associated component of the fluid processing device to a monitoring position based at least in part on the signal.

In another aspect, a method is provided for adjusting the position of a light source of a detection assembly including a light source and a light detector, with the light source being associated with a component of a fluid processing device and provided in an initial position with respect to the associated component of the fluid processing device. The method includes emitting a light from the light source, receiving at least a portion of the light with the light detector and generating a signal indicative of the amount of light received by the light detector, and moving the light source with respect to the associated component of the fluid processing device to a monitoring position based at least in part on the signal.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

FIGS. 1-34 illustrate components and aspects of a blood or fluid processing system that embodies various aspects of the present subject matter. While the system may be described herein in terms of its use in separating blood into two or more components, it should be understood that systems according to the present disclosure can be used for processing a variety of biological or bodily fluids (including fluids containing both bodily and non-bodily fluids, such as anticoagulated blood), as well as non-bodily fluids.

Figure 1:
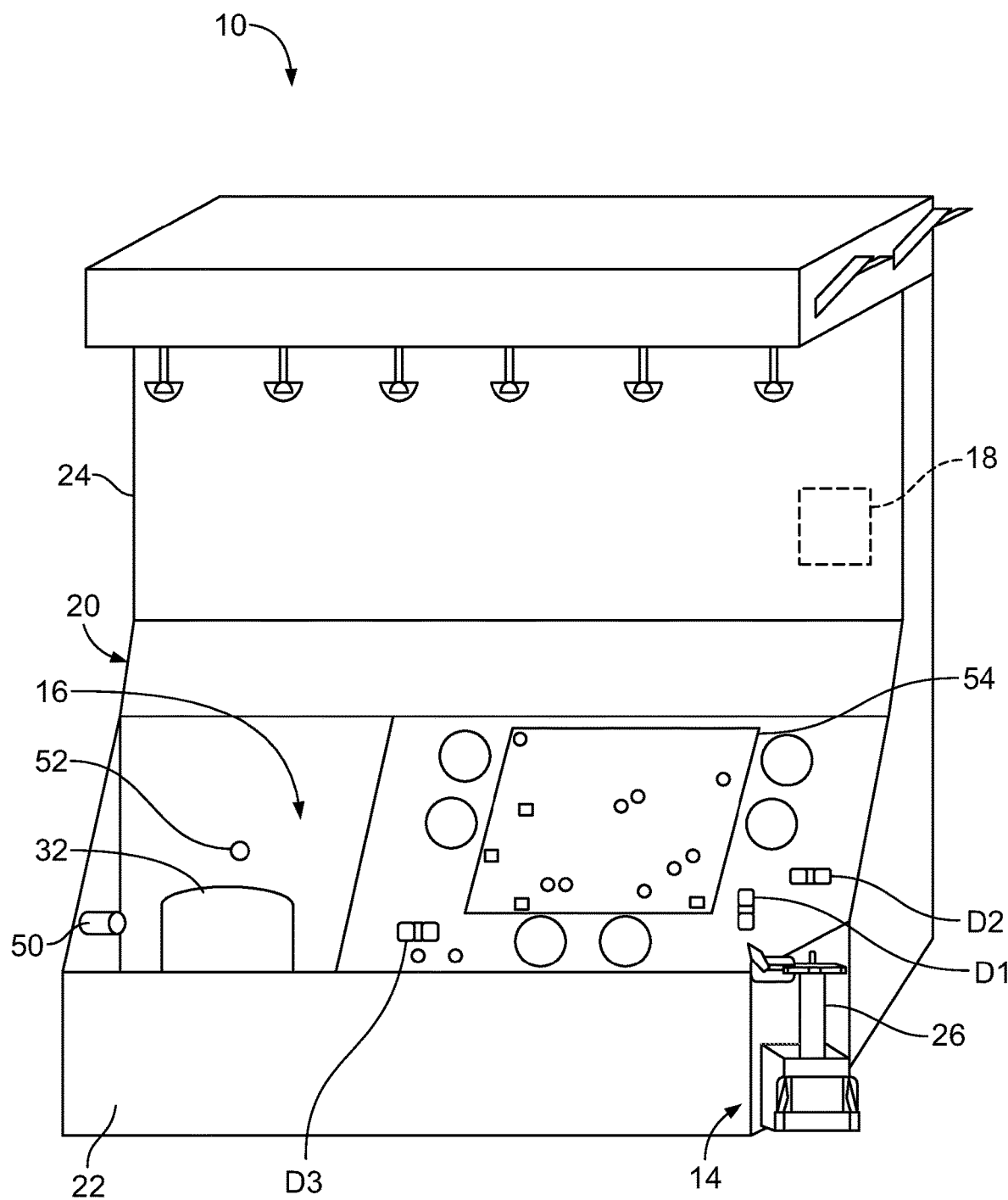
FIG. 1 is a perspective view of an exemplary fluid processing device that comprises a component of a fluid processing system according to an aspect of the present disclosure.
Figure 2:
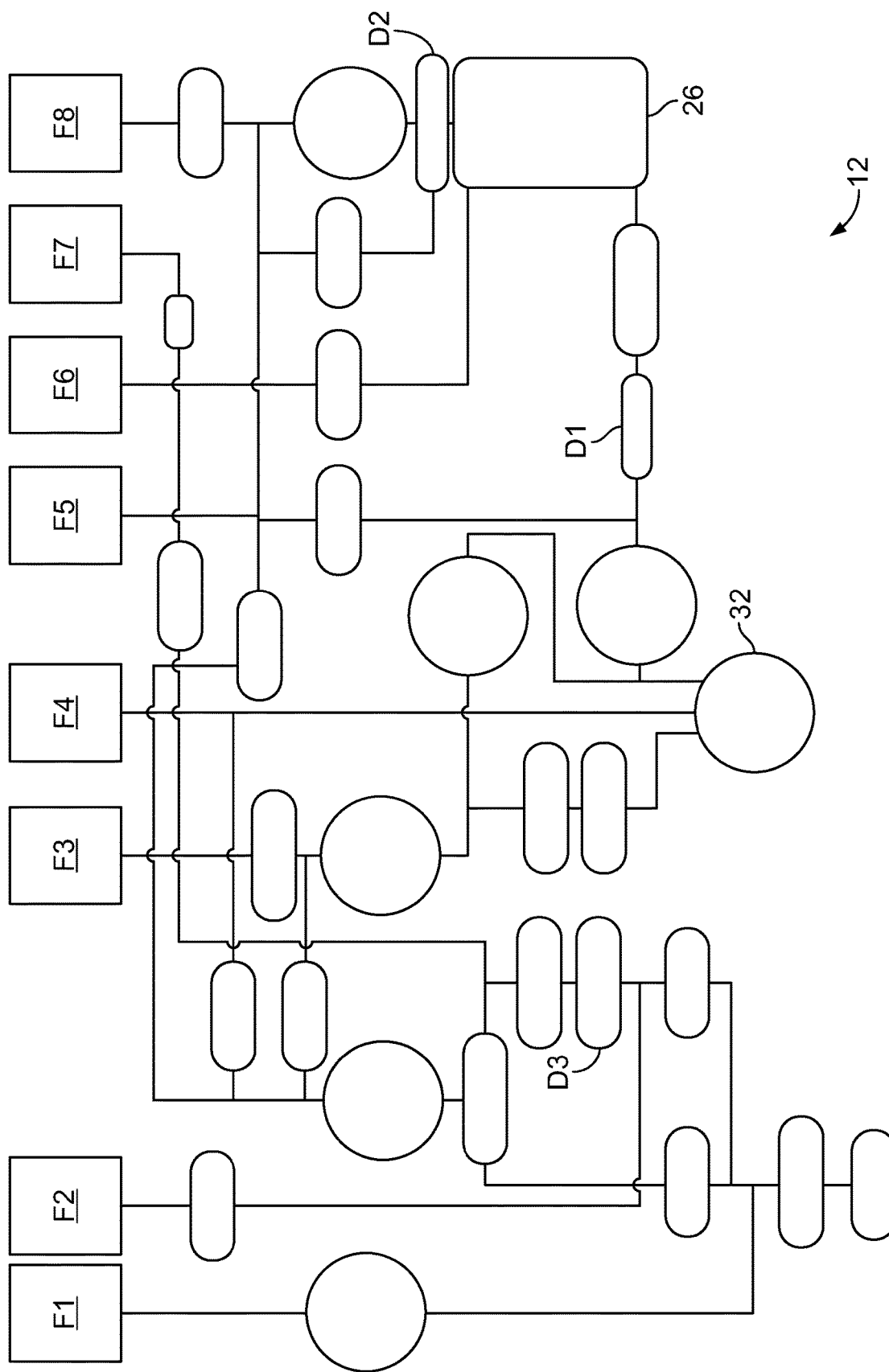
FIG. 2 is a schematic view of an exemplary disposable fluid flow circuit that may be mounted to the fluid processing device of FIG. 1 to complete a fluid processing system according to an aspect of the present disclosure.

Fluid processing systems according to the present disclosure typically include two principal components, a durable and reusable fluid processing device 10 (FIG. 1) and a disposable fluid flow circuit 12 (FIG. 2). While a disposable fluid flow circuit 12 may be advantageous for processing bodily fluids, it should be understood that the principles described herein are applicable to non-bodily fluids, in which case a disposable fluid flow circuit may be omitted.

The illustrated fluid processing device 10 includes a spinning membrane separator drive unit 14 (FIG. 1), a centrifuge or centrifugal separator 16 (FIG. 3), additional components that control fluid flow through the disposable flow circuit 12, and a controller 18 (FIG. 1), which governs the operation of the other components of the fluid processing device 10 (including a detection assembly) to perform a procedure selected by the operator. The principles described herein regarding adjustment of the light source of a detection assembly are not limited to any particular fluid processing systems or procedures, so no complete fluid processing devices or procedures will be described in detail herein. However, reference may be made to PCT Patent Application Publication No. WO 2018/053217 A1 for a detailed description of the fluid processing device 10 of FIG. 1, along with various exemplary procedures that may be carried out using such a system.

I. The Durable Fluid Processing Device

The fluid processing device 10 (FIG. 1) is configured as a durable item that is capable of long-term use. It should be understood that the fluid processing device 10 of FIG. 1 is merely exemplary of one possible configuration and that fluid processing devices according to the present disclosure may be differently configured.

In the illustrated embodiment, the fluid processing device 10 is embodied in a single housing or case 20. The illustrated case 20 includes a generally horizontal portion 22 (which may include an inclined or angled face or upper surface for enhanced visibility and ergonomics) and a generally vertical portion 24. The spinning membrane separator drive unit 14 and the centrifugal separator 16 are shown as being incorporated into the generally horizontal portion 22 of the case 20, while the controller 18 is shown as being incorporated into the generally vertical portion 24.

A. Spinning Membrane Separator Drive Unit

The illustrated fluid processing device 10 includes a spinner support or spinning membrane separator drive unit 14 (FIG. 1) for accommodating a generally cylindrical spinning membrane separator 26 of a fluid flow circuit 12 (FIG. 2). U.S. Pat. No. 5,194,145 (which is hereby incorporated herein by reference) describes an exemplary spinning membrane separator drive unit that would be suitable for incorporation into the fluid processing device 10, but it should be understood that the spinning membrane separator drive unit 14 may be differently configured without departing from the scope of the present disclosure.

Typically, a spinning membrane separator is not monitored by a detection assembly having a light source, so the principles described herein regarding adjustment of the position of a light source of a detection assembly may be more applicable to the centrifugal separator 16. However, conduits leading into and/or exiting from a spinning membrane separator may be monitored by a detection assembly having a light source, so the light source adjustment principles described herein may be applicable to such detection assemblies. Additionally, to the extent that a spinning membrane would be monitored by a detection assembly having a light source, the light source adjustment principles described herein may be applicable to such a detection assembly.

B. Centrifugal Separator

Adjustment of the position of a light source of a detection assembly is described herein in the context of a detection assembly of the centrifugal separator 16. Accordingly, a particularly configured centrifugal separator 16 and associated centrifugal separation chamber 32 and detection assembly will be described herein for illustrative purposes. However, it should be understood that such principles may be practiced in combination with any configuration of a centrifugal separator 16 or in the absence of a centrifugal separator.

Figure 3:
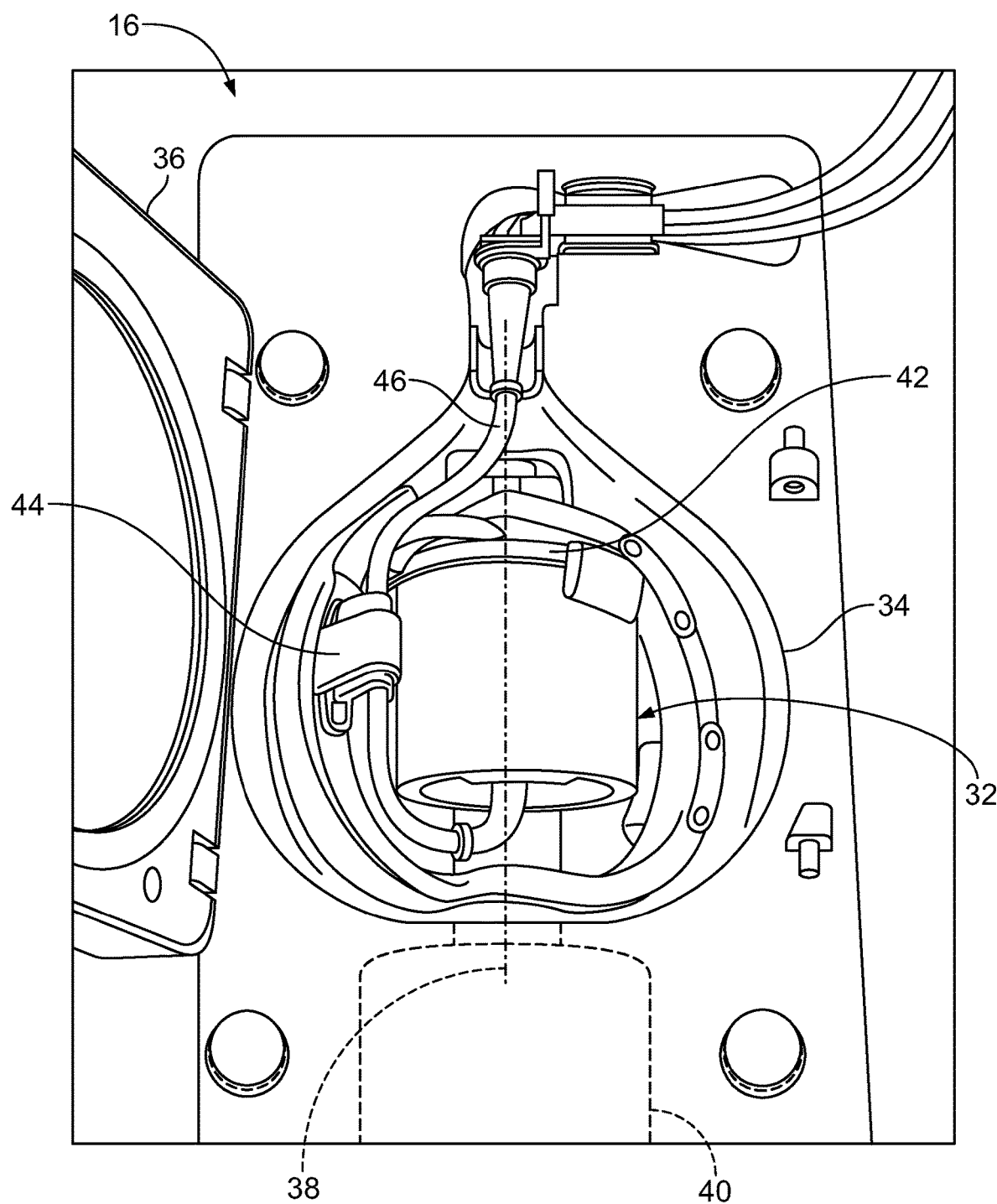
FIG. 3 is a perspective view of an exemplary centrifugal separator of the fluid processing device of FIG. 1, with the centrifugal separation chamber of a fluid flow circuit mounted therein.

The illustrated centrifugal separator 16 includes a centrifuge compartment 34 that may receive the other components of the centrifugal separator 16 (FIG. 3). The centrifuge compartment 34 may include a lid 36 that is opened to insert and remove a centrifugal separation chamber 32 of the fluid flow circuit 12. During a separation procedure, the lid 36 may be closed with the centrifugal separation chamber 32 positioned within the centrifuge compartment 34, as the centrifugal separation chamber 32 is spun or rotated about an axis 38 under the power of an electric drive motor or rotor 40 of the centrifugal separator 16.

Figure 4:
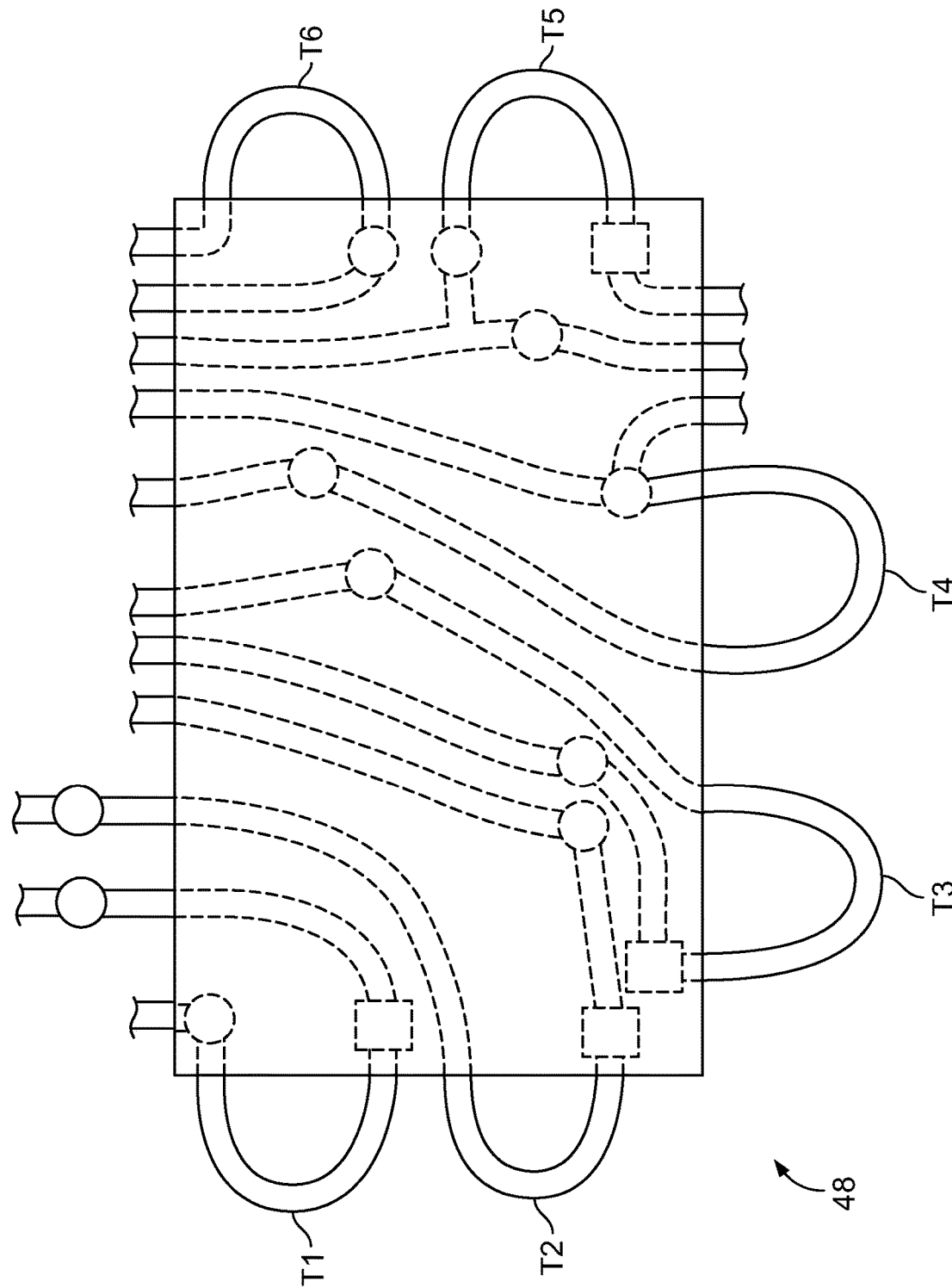
FIG. 4 is a top plan view of an exemplary cassette of a fluid flow circuit, which can be actuated to perform a variety of different fluid processing procedures in association with the fluid processing device shown in FIG. 1.

The particular configuration and operation of the centrifugal separator 16 depends upon the particular configuration of the centrifugal separation chamber 32 of the fluid flow circuit 12. In one embodiment, the centrifugal separator 16 is similar in structure and operation to that of the ALYX system manufactured by Fenwal, Inc. of Lake Zurich, Ill., which is an affiliate of Fresenius Kabi AG of Bad Homburg, Germany, as described in greater detail in U.S. Pat. No. 8,075,468, which is hereby incorporated herein by reference. More particularly, the centrifugal separator 16 may include a carriage or support 42 that holds the centrifugal separation chamber 32 and a yoke member 44. The yoke member 44 engages an umbilicus 46 of the fluid flow circuit 12, which extends between the centrifugal separation chamber 32 and a cassette 48 of the fluid flow circuit 12 (FIG. 4). The yoke member 44 causes the umbilicus 46 to orbit around the centrifugal separation chamber 32 at a one omega rotational speed. The umbilicus 46 twists about its own axis as it orbits around the centrifugal separation chamber 32. The twisting of the umbilicus 46 about its axis as it rotates at one omega with the yoke member 44 imparts a two omega rotation to the centrifugal separation chamber 32, according to known design. The relative rotation of the yoke member 44 at a one omega rotational speed and the centrifugal separation chamber 32 at a two omega rotational speed keeps the umbilicus 46 untwisted, avoiding the need for rotating seals.

Figure 6:
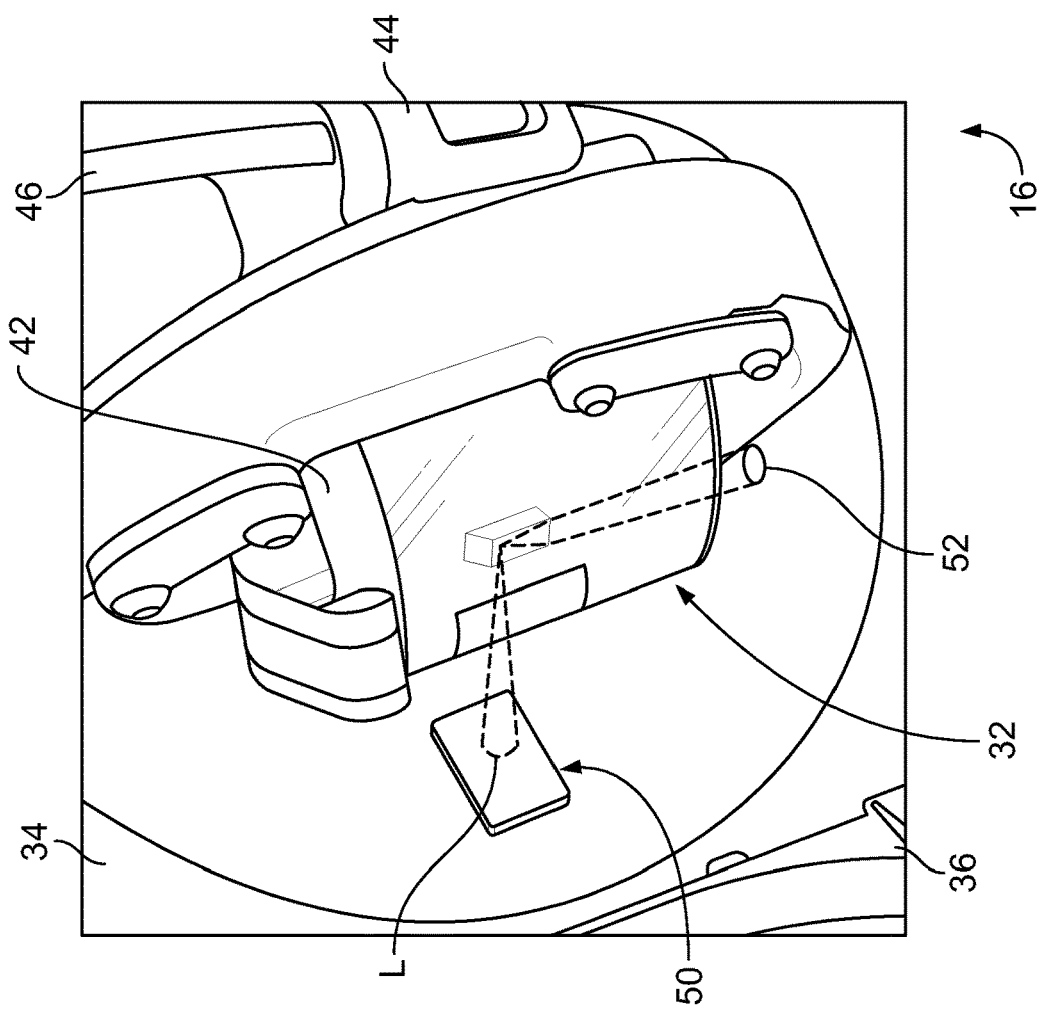
FIG. 6 is a perspective view of the centrifugal separator of FIG. 3, with the light source operating to transmit a light beam to a light detector of the interface monitoring assembly.
Figure 5:
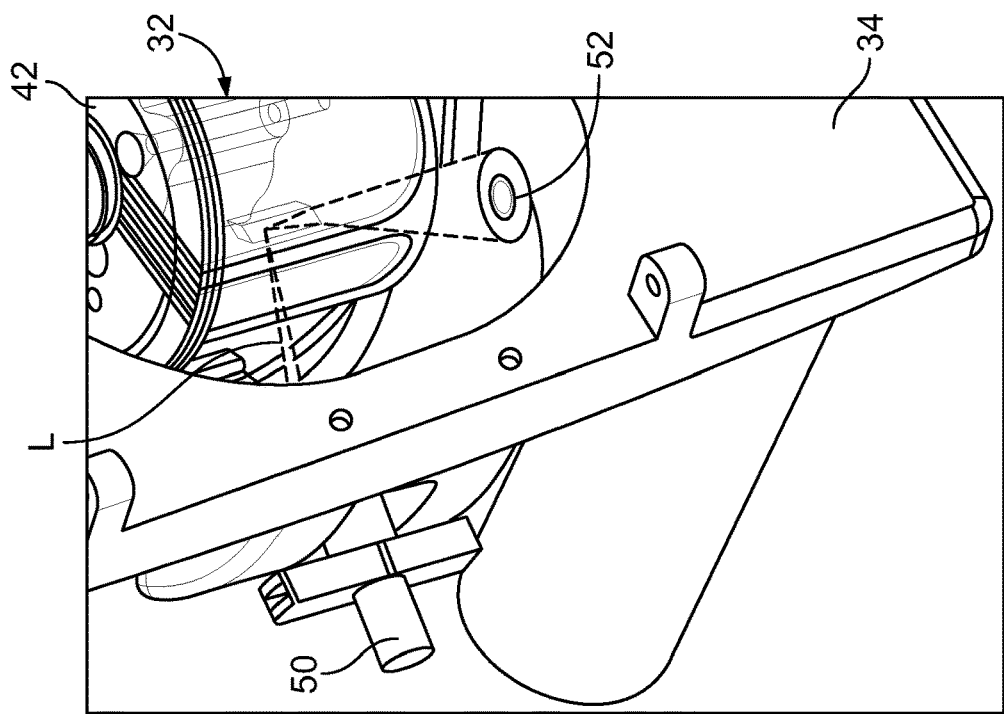
FIG. 5 is a perspective view of the centrifugal separator of FIG. 3, with selected portions thereof broken away to show a light source of an interface monitoring assembly.
Figure 7:
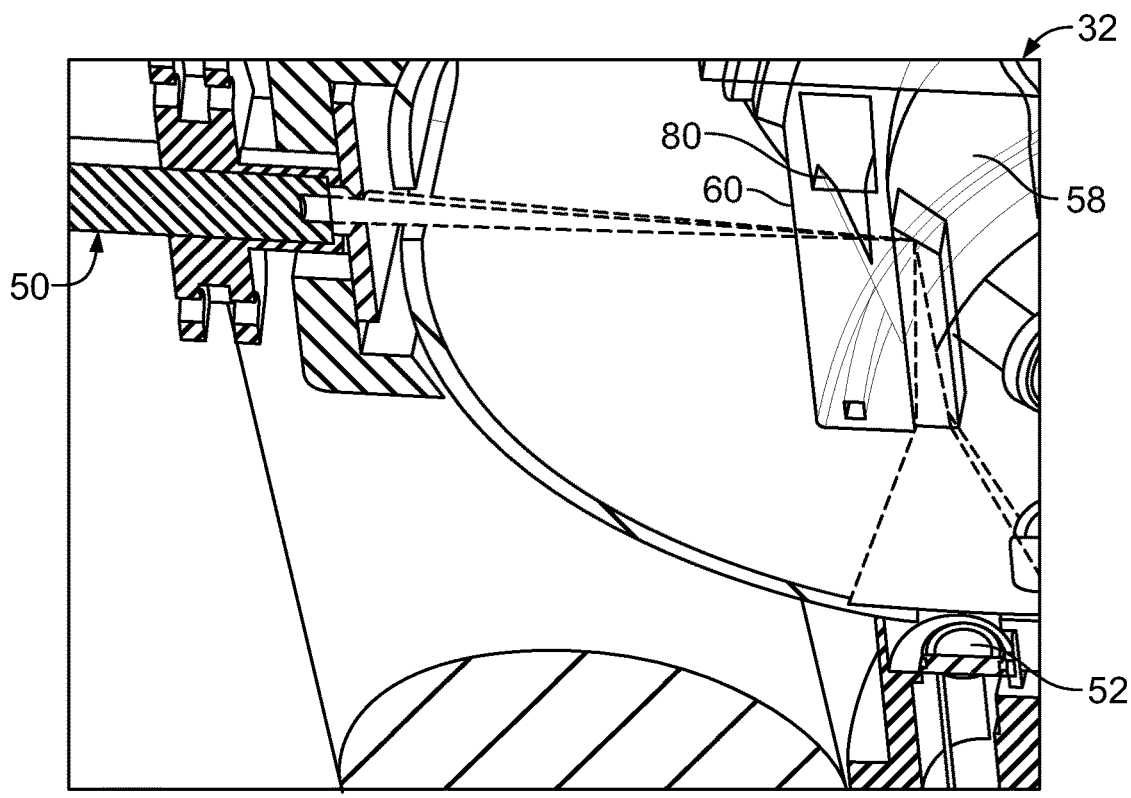
FIG. 7 is a perspective view of the centrifugal separator of FIG. 3, with selected portions thereof broken away to show the light source and light detector of the interface monitoring assembly.

A fluid is introduced into the centrifugal separation chamber 32 by the umbilicus 46, with the fluid being separated (e.g., into a layer of less dense components, such as platelet-rich plasma, if the fluid is blood, and a layer of more dense components, such as packed red blood cells, if the fluid is blood) within the centrifugal separation chamber 32 as a result of centrifugal forces as it rotates. Components of an interface monitoring assembly may be positioned within the centrifuge compartment 16 to oversee separation of fluid within the centrifugal separation chamber 32. As shown in FIGS. 5-7, the interface monitoring assembly may include a light source 50 and a light detector 52, which is positioned and oriented to receive at least a portion of the light emitted by the light source 50. The illustrated light source 50 and light detector 52 are associated with stationary surfaces of the centrifuge compartment 34, but either or both may instead be associated with a movable structure or component of the fluid processing device 10, as in U.S. Pat. No. 5,316,667, which is hereby incorporated herein by reference. Further, as will be described in greater detail herein, the position of the light source 50 may be adjusted with respect to the structure or component of the fluid processing device 10 with which it is associated according to an aspect of the present disclosure.

The initial or default orientation and position of the various components of the interface monitoring assembly depend at least in part on the particular configuration of the centrifugal separation chamber 32. In general, though, the light source 50 emits a light beam "L" (e.g., a laser light beam) through the separated fluid components within the centrifugal separation chamber 32 (which may be formed of a material that substantially transmits the light L or at least a particular wavelength of the light L without absorbing it). A portion of the light L reaches the light detector 52, which transmits a signal to the controller 18 that is indicative of the location of an interface between the separated fluid components. If the controller 18 determines that the interface is in the wrong location (which can affect the separation efficiency of the centrifugal separator 16 and/or the quality of the separated blood components), then it can issue commands to the appropriate components of the fluid processing device 10 to modify their operation so as to move the interface to the proper location.

C. Other Components of the Fluid Processing Device

In addition to the spinning membrane separator drive unit 14 and the centrifugal separator 16, the fluid processing device 10 may include other components compactly arranged to aid fluid processing. Exemplary components (including a pump system, a cassette station 54 to accommodate the cassette 48 of the fluid flow circuit 12) are described in greater detail in PCT Patent Application Publication No. WO 2018/053217 A1.

Among the various components of the fluid processing device 10 are a plurality of detection assemblies D1-D3. While the adjustment principles described herein are presented with reference to the interface monitoring assembly of the centrifugal separator 16, it should be understood that similar principles may be applied to the other detection assemblies D1-D3, as well as detection assemblies that are differently configured from the ones described herein.

One of the detection assemblies comprises a centrifuge outlet sensor D1 for determining one or more properties of fluids flowing out of the centrifugal separator 16. If the fluid flowing out of the centrifugal separator 16 includes red blood cells, the centrifuge outlet sensor D1 may be configured to determine the hematocrit of the fluid. If the fluid flowing out of the centrifugal separator 16 is platelet-rich plasma, the centrifuge outlet sensor D1 may be configured to determine the platelet concentration of the platelet-rich plasma. The centrifuge outlet sensor D1 may detect the one or more properties of a fluid by optically monitoring the fluid as it flows through tubing of the fluid flow circuit 12 or by any other suitable approach. The controller 18 may receive signals from the centrifuge outlet sensor D1 that are indicative of the one or more properties of fluid flowing out of the centrifugal separator 16 and use the signals to optimize the procedure based upon that property or properties.

Another one of the detection assemblies comprises a spinner outlet sensor D2, which accommodates tubing of a fluid flow circuit 12 that flows a separated fluid component out of a spinning membrane separator 26 of the fluid flow circuit 12.

A third one of the detection assemblies comprises an air detector D3 (e.g., an ultrasonic bubble detector), which accommodates tubing of the fluid flow circuit 12 that flows fluid to a recipient. It may be advantageous to prevent air from reaching the recipient, so the air detector D3 may transmit signals to the controller 18 that are indicative of the presence or absence of air in the tubing. If the signal is indicative of air being present in the tubing, the controller 18 may initiate an alarm or error condition to alert an operator to the condition and/or to take corrective action to prevent the air from reaching the recipient (e.g., by reversing the flow of fluid through the tubing or diverting flow to a vent location).

D. Controller

As described above, the fluid processing device 10 includes a controller 18, which is suitably configured and/or programmed to control operation of the fluid processing device 10. In one embodiment, the controller 18 comprises a main processing unit (MPU), which can comprise, e.g., a PENTIUM® type microprocessor made by Intel Corporation, although other types of conventional microprocessors can be used. In one embodiment, the controller 18 may be mounted inside the generally vertical portion 24 of the case 20, adjacent to or incorporated into an operator interface station (e.g., a touchscreen). In other embodiments, the controller 18 and operator interface station may be associated with the generally horizontal portion 22 or may be incorporated into a separate device that is connected (either physically, by a cable or the like, or wirelessly) to the fluid processing device 10.

The controller 18 is configured and/or programmed to execute at least one fluid processing application but, more advantageously, is configured and/or programmed to execute a variety of different fluid processing applications. For example, the controller 18 may be configured and/or programmed to carry out one or more of the following: a double unit red blood cell collection procedure, a plasma collection procedure, a plasma/red blood cell collection procedure, a red blood cell/platelet/plasma collection procedure, a platelet collection procedure, a platelet/plasma collection procedure, and a mononuclear cell collection procedure. Additional or alternative procedure applications (e.g., plasma exchange, red blood cell exchange, and photopheresis) can be included without departing from the scope of the present disclosure.

More particularly, in carrying out any one of these fluid processing applications, the controller 18 is configured and/or programmed to control one or more of the following tasks: drawing fluid into a fluid flow circuit 12 mounted to the fluid processing device 10, conveying fluid through the fluid flow circuit 12 to a location for separation (i.e., into the spinning membrane separator 26 or the centrifugal separation chamber 32 of the fluid flow circuit 12), separating the fluid into two or more components as desired, and conveying the separated components into storage containers, to a second location for further separation (e.g., into whichever of the spinning membrane separator 26 and centrifugal separation chamber 32 that was not used in the initial separation stage), or to a recipient (which may be the source from which the fluid was originally drawn).

This may include instructing the spinning membrane separator drive unit 14 and/or the centrifugal separator 16 to operate at a particular rotational speed and instructing a pump to convey fluid through a portion of the fluid flow circuit 12 at a particular flow rate. Hence, while it may be described herein that a particular component of the fluid processing device 10 (e.g., the spinning membrane separator drive unit 14 or the centrifugal separator 16) performs a particular function, it should be understood that that component is being controlled by the controller 18 to perform that function.

Before, during, and after a procedure, the controller 18 may receive signals from various components of the fluid processing device 10 to monitor various aspects of the operation of the fluid processing device 10 and characteristics of the fluid and separated fluid components as they flow through the fluid flow circuit 12. If the operation of any of the components and/or one or more characteristics of the fluid or separated fluid components is outside of an acceptable range, then the controller 18 may initiate an alarm or error condition to alert the operator and/or take action to attempt to correct the condition. The appropriate corrective action will depend upon the particular error condition and may include action that is carried out with or without the involvement of an operator.

For example, the controller 18 may include an interface control module, which receives signals from the light detector 52 of the interface monitoring assembly and the centrifuge outlet sensor D1. The signals that the controller 18 receives from the light detector 52 are indicative of the location of an interface between the separated fluid components within the centrifugal separation chamber 32, while the signals from the centrifuge outlet sensor D1 indicate whether the target interface location should be adjusted. If the controller 18 determines that the interface is in the wrong location, then it can issue commands to the appropriate components of the fluid processing device 10 to modify their operation so as to move the interface to the proper location. For example, the controller 18 may instruct a pump to cause blood to flow into the centrifugal separation chamber 32 at a different rate and/or for a separated fluid component to be removed from the centrifugal separation chamber 32 at a different rate and/or for the centrifugal separation chamber 32 to be spun at a different speed by the centrifugal separator 16.

As will be described in greater detail, the controller 18 may oversee a calibration procedure in which the position of the light source of a detection assembly is adjusted for improved performance.

II. The Disposable Fluid Flow Circuit

A. Overview

As for the fluid flow circuit or flow set 12 (FIG. 2), it is intended to be a sterile, single use, disposable item. Before beginning a given procedure, the operator loads various components of the fluid flow circuit 12 in the case 20 in association with the fluid processing device 10. Proper operation of the various detection assemblies of the fluid processing device 10 may depend upon proper orientation of the fluid flow circuit 12 with respect to the detection assemblies, such that care should be taken when mounting the fluid flow circuit 12 to the fluid processing device 10. However, in the event that one or more of the components of the fluid flow circuit 12 is not properly oriented with respect to an associated detection assembly of the fluid processing device 10, the position of the light source of that detection assembly may be adjusted to improve performance of the detection assembly. While improper installation or misalignment of a fluid flow circuit 12 may be a common reason for adjusting the position of the light source of a detection assembly, it should be understood that other reasons exist, such that the principles described herein are not limited to use in fluid processing systems employing a disposable fluid flow circuit.

Once the fluid flow circuit 12 is mounted to the fluid processing device 10, the controller 18 implements a procedure based upon preset protocols, taking into account other input from the operator. Upon completing the procedure, the operator removes the fluid flow circuit 12 from association with the fluid processing device 10. The portions of the fluid flow circuit 12 holding the collected fluid component or components (e.g., collection containers or bags) are removed from the case 20 and retained for storage, immediate use, or further processing. The remainder of the fluid flow circuit 12 is removed from the case 20 and discarded.

A variety of different disposable fluid flow circuits may be used in combination with the fluid processing device 10, with the appropriate fluid flow circuit depending on the procedure to be carried out using the system. Generally speaking, though, the fluid flow circuit 12 includes a cassette 48 (FIG. 4) to which the other components of the fluid flow circuit 12 are connected by flexible tubing. In one embodiment, the cassette 48 is similarly configured to the cassette of U.S. Pat. No. 5,868,696 (which is hereby incorporated herein by reference), but is adapted to include additional components (e.g., more tubing loops T1-T6) and functionality.

The other components may include a plurality of fluid containers F1-F8 (for holding fluid to be processed, a separated fluid component, an intravenous fluid, or an additive solution, for example), one or more fluid source access devices (e.g., a connector for accessing fluid within a fluid container), and a spinning membrane separator 26 and/or a centrifugal separation chamber 32 (FIG. 2).

B. Centrifugal Separation Chamber

Figure 8:
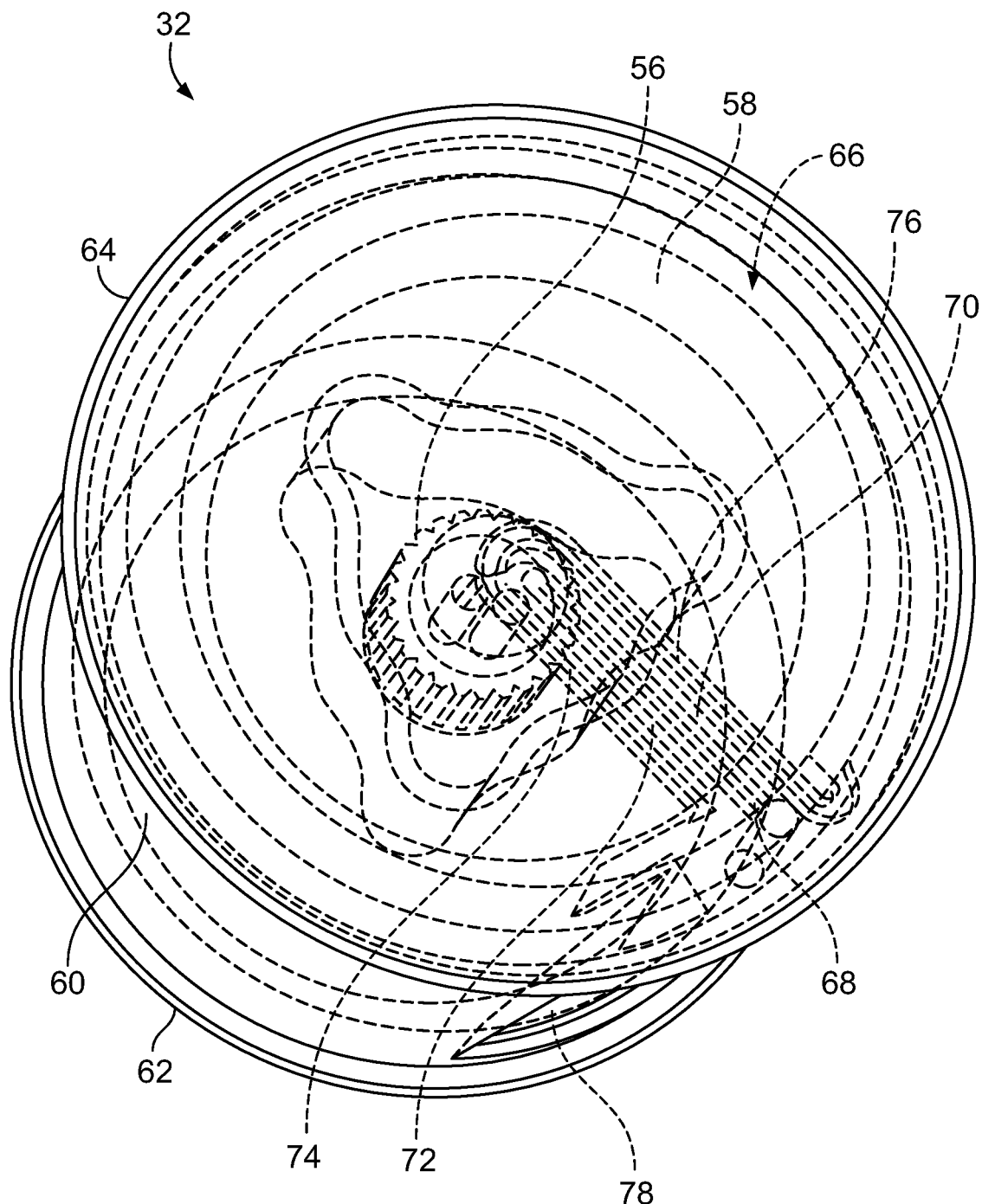
FIG. 8 is a perspective view of an exemplary centrifugal separation chamber of a fluid flow circuit.
Figure 9:
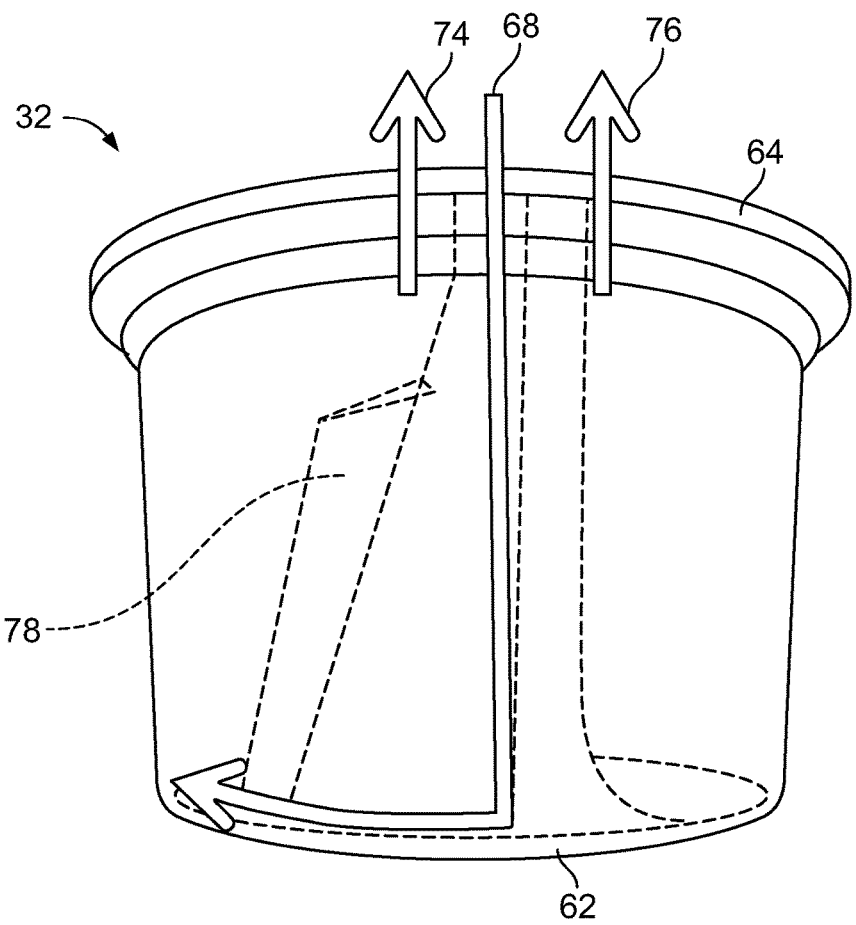
FIG. 9 is a front elevational view of the centrifugal separation chamber of FIG. 8.
Figure 10:
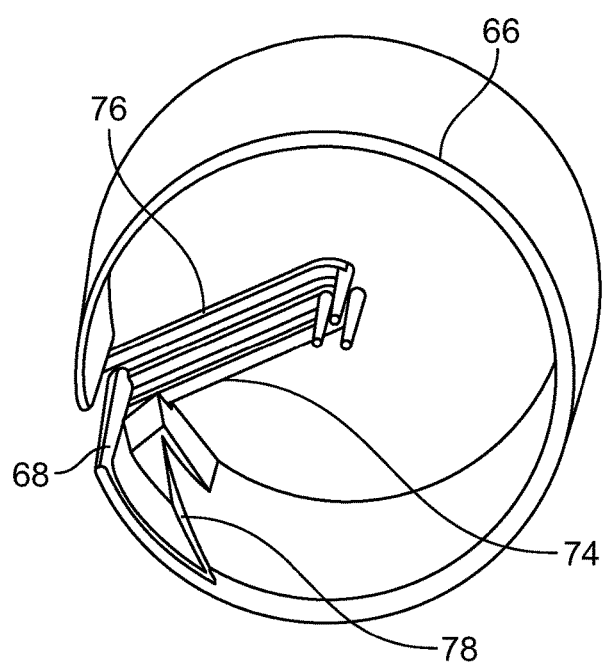
FIG. 10 is a bottom perspective view of the fluid flow path through the centrifugal separation chamber of FIG. 8.

An exemplary centrifugal separation chamber 32 is shown in FIGS. 8 and 9, while FIG. 10 illustrates the fluid flow path defined by the centrifugal separation chamber 32. In the illustrated embodiment, the body of the centrifugal separation chamber 32 is pre-formed in a desired shape and configuration (e.g., by injection molding) from a rigid, biocompatible plastic material, such as a non-plasticized medical grade acrylonitrile-butadiene-styrene (ABS). All contours, ports, channels, and walls that affect the fluid separation process are preformed in a single, injection molded operation. Alternatively, the centrifugal separation chamber 32 can be formed by separate molded parts, either by nesting cup-shaped subassemblies or two symmetric halves.

The underside of the centrifugal separation chamber 32 includes a shaped receptacle 56 that is suitable for receiving an end of the umbilicus 46 of the fluid flow circuit 12 (FIG. 3). A suitable receptacle 56 and the manner in which the umbilicus 46 may cooperate with the receptacle 56 to deliver fluid to and remove fluid from the centrifugal separation chamber 32 are described in greater detail in U.S. Pat. No. 8,075,468.

The illustrated centrifugal separation chamber 32 has radially spaced apart inner (low-g) and outer (high-g) side wall portions 58 and 60, a bottom or first end wall portion 62, and a cover or second end wall portion 64. The cover 64 comprises a simple flat part that can be easily welded or otherwise secured to the body of the centrifugal separation chamber 32. The wall portions 58 and 60, the bottom 62, and the cover 64 together define an enclosed, generally annular channel 66 (FIG. 10).

An inlet 68 communicating with the channel 66 is defined between opposing interior radial walls 70 and 72. One of the interior walls 70 joins the outer (high-g) wall portion 60 and separates the upstream and downstream ends of the channel 66. The interior walls 70 and 72 define the inlet passageway 68 of the centrifugal separation chamber 32 which, in one flow configuration, allows fluid to flow from the umbilicus 46 to the upstream end of the channel 66.

The illustrated centrifugal separation chamber 32 further includes first and second outlets 74 and 76, respectively, which may be defined by opposing surfaces of interior radial walls. Both the first and second outlets 74 and 76 extend radially inward from the channel 66. The first outlet 74 extends radially inward from an opening which, in the illustrated embodiment, is located at the inner side wall portion 58, while the second outlet 76 extends radially inward from an opening that is associated with the outer side wall portion 60. The illustrated first outlet 74 is positioned adjacent to the inlet 68 (near the upstream end of the channel 66), while the second outlet 76 may be positioned at the opposite, downstream end of the channel 66.

It should be understood that the centrifugal separation chamber 32 illustrated in FIG. 8 is merely exemplary and that the centrifugal separation chamber 32 may be differently configured without departing from the scope of the present disclosure. For example, PCT Patent Application Publication No. WO 2018/053217 A1 describes other exemplary centrifugal separation chamber configurations. Additionally, as noted above, while the principles regarding adjustment of the position of the light source of a detection assembly are described herein in the context of a detection assembly that monitors fluid separation within the centrifugal separation chamber 32, it should be understood that such principles are applicable to detection assemblies configured to monitor other subjects.

1. Centrifugal Separation and Interface Detection Principles

Fluid flowed into the channel 66 separates into an optically dense layer "R" and a less optically dense layer "P" (FIGS. 11-13) as the centrifugal separation chamber 32 is rotated about the rotational axis 38. The optically dense layer R forms as larger and/or heavier fluid particles move under the influence of centrifugal force toward the outer (high-g) wall portion 60. If the fluid being separated is blood, the optically dense layer R will typically include red blood cells but, depending on the speed at which the centrifugal separation chamber 32 is rotated, other cellular components (e.g., larger white blood cells) may also be present in the optically dense layer R.

If the fluid being separated is blood, the less optically dense layer P typically includes a plasma constituent, such as platelet-rich plasma or platelet-poor plasma. Depending on the speed at which the centrifugal separation chamber 32 is rotated and the length of time that the blood is resident therein, other components (e.g., smaller white blood cells and anticoagulant) may also be present in the less optically dense layer P.

In one embodiment, fluid introduced into the channel 66 via the inlet 68 will travel in a generally clockwise direction (in the orientation of FIG. 8) as the optically dense layer R separates from the less optically dense layer P. The optically dense layer R continues moving in the clockwise direction as it travels the length of the channel 66 along the outer side wall portion 60, from the upstream end to the downstream end, where it exits the channel 66 via the second outlet 76. The less optically dense layer P separated from the optically dense layer R reverses direction, moving counterclockwise along the inner side wall portion 58 to the first outlet 74, adjacent to the inlet 68.

Figure 11:
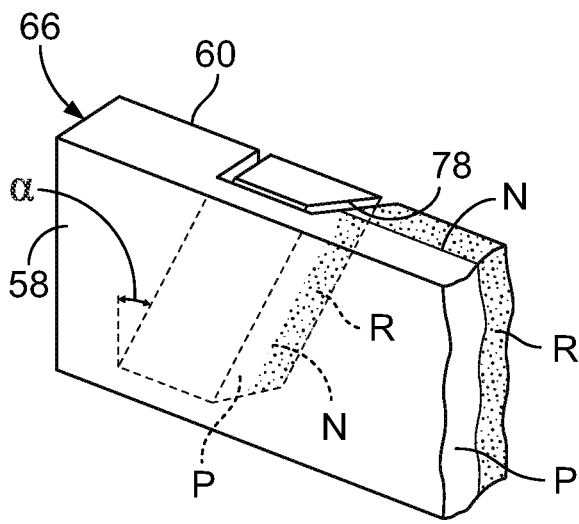
FIG. 11 is an enlarged perspective view of a portion of a channel of the centrifugal separation chamber of FIGS. 8-10, with an interface between separated fluid components being positioned at a (typically) desired location on a ramp defined within the channel.
Figure 12:
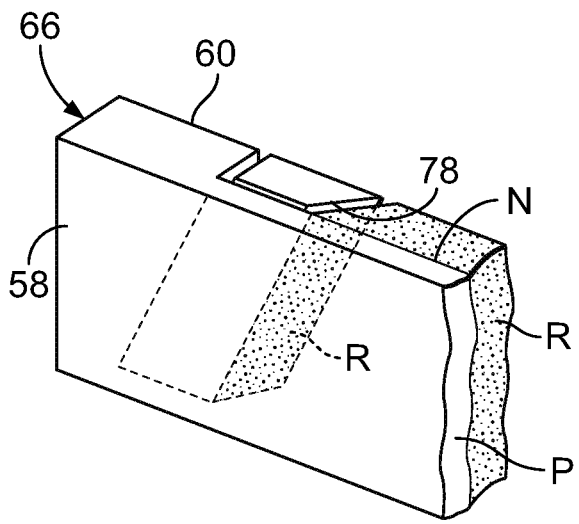
FIG. 12 is an enlarged perspective view of the channel and ramp of FIG. 11, with the interface being at a (typically) undesired high location on the ramp.
Figure 13:
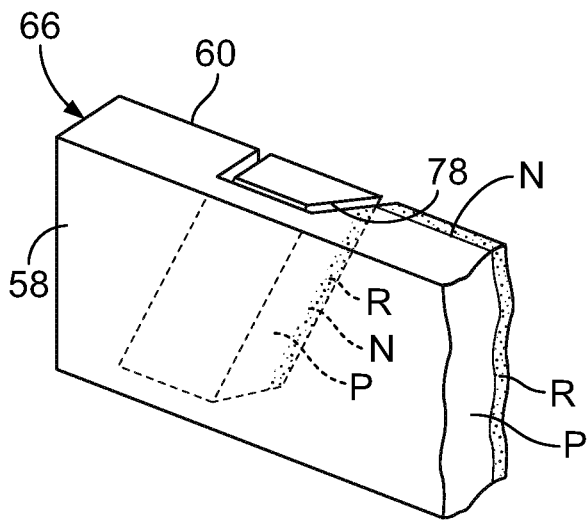
FIG. 13 is an enlarged perspective view of the channel and ramp of FIG. 11, with the interface being at a (typically) undesired low location on the ramp.

The transition between the optically dense layer R and the less optically dense layer P may be referred to as the interface "N". If the fluid being separated is blood, the interface N contains mononuclear cells and peripheral blood stem cells. The location of the interface N within the channel 66 of the centrifugal separation chamber 32 can dynamically shift during fluid processing, as FIGS. 11-13 show. If the location of the interface N is too high (that is, if it is too close to the inner side wall portion 58 and the first outlet 74, as in FIG. 12), red blood cells can flow into the first outlet 74, potentially adversely affecting the quality of the low density components (platelet-rich plasma or platelet-poor plasma). On the other hand, if the location of the interface N is too low (that is, if it resides too far away from the inner wall portion 58, as FIG. 13 shows), the collection efficiency of the system may be impaired. The ideal or target interface location may be experimentally determined, which may vary depending on any of a number of factors (e.g., the configuration of the centrifugal separation chamber 32, the rate at which the centrifugal separation chamber 32 is rotated about the rotational axis 38, etc.).

As described above, the fluid processing device 10 may include an interface monitoring assembly (including the light source 50 and the light detector 52), a centrifuge outlet sensor D1, and a controller 18 with an interface control module to monitor and, as necessary, adjust or correct the position of the interface N. In the illustrated embodiment, the centrifugal separation chamber 32 is formed with a ramp 78 extending from the high-g wall portion 60 at an angle α across at least a portion of the channel 66 (FIGS. 8 and 11-13). The angle α, measured with respect to the rotational axis 38 is about 25° in one embodiment. FIGS. 11-13 show the orientation of the ramp 78 when viewed from the low-g side wall portion 58 of the centrifugal separation chamber 32. Although it describes a flexible separation chamber, the general structure and function of the ramp 78 may be better understood with reference to U.S. Pat. No. 5,632,893, which is hereby incorporated herein by reference.

The ramp 78 makes the interface N between the optically dense layer R and the less optically dense layer P more discernible for detection, displaying the optically dense layer R, less optically dense layer P, and interface N for viewing through a light-transmissive portion of the centrifugal separation chamber 32. To that end, the ramp 78 and at least the portion of the centrifugal separation chamber 32 angularly aligned with the ramp 78 may be formed of a light-transmissive material, although it may be advantageous for the entire centrifugal separation chamber 32 to be formed of the same light-transmissive material.

In the illustrated embodiment, the light source 50 of the interface monitoring system is associated with a fixture or wall of the centrifuge compartment 34 and oriented to emit a light L that is directed toward the rotational axis 38 of the centrifugal separator 16, as shown in FIGS. 5-7. If the light detector 52 is positioned at an angle with respect to the light source 50 (as in the illustrated embodiment), the light L emitted by the light source 50 must be redirected from its initial path before it will reach the light detector 52. In the illustrated embodiment, the light L is redirected by a reflector that is associated with a light-transmissive portion of the inner side wall portion 58, as shown in FIGS. 5 and 6. The reflector may be a separate piece that is secured to the inner side wall portion 58 (e.g., by being bonded thereto) or may be integrally formed with the body of the centrifugal separation chamber 66.

Figures 14, 15:
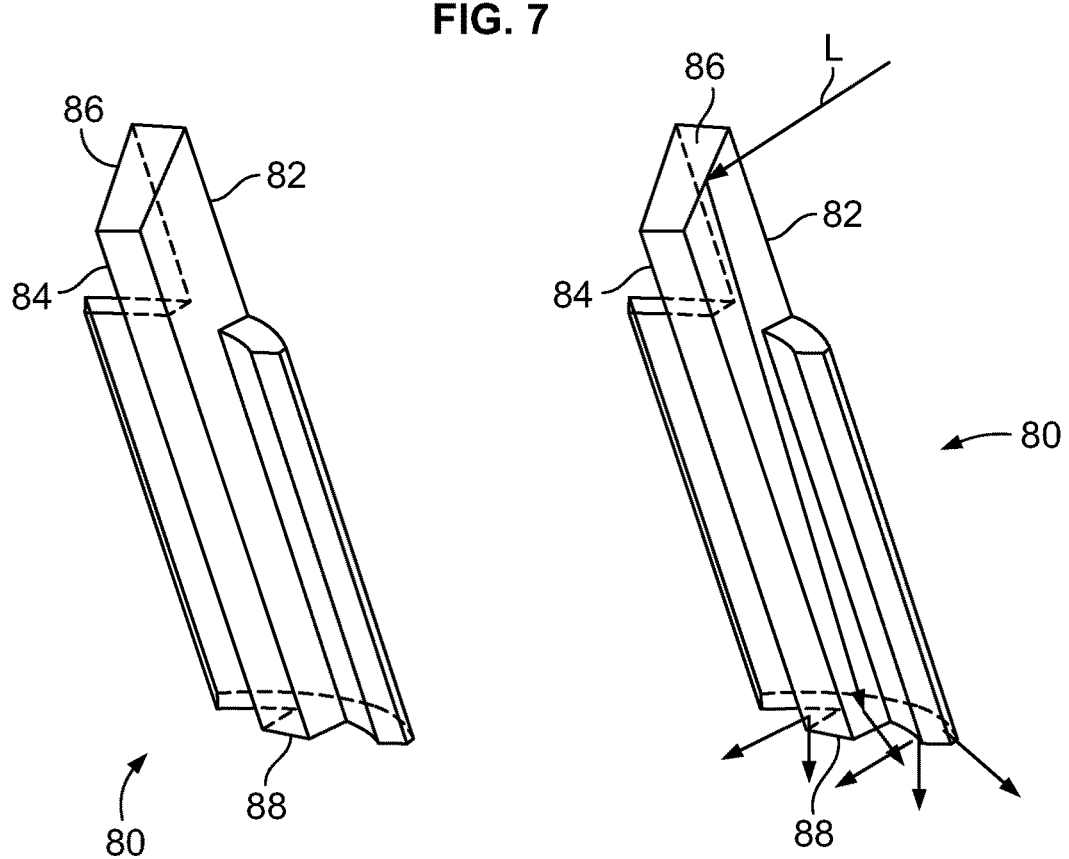
FIG. 14 is a perspective view of a prismatic reflector used in combination with the centrifugal separation chamber of FIGS. 8-10.
FIG. 15 is a perspective view of the prismatic reflector of FIG. 14, showing light being transmitted therethrough.

In one embodiment, the reflector may be a reflective surface, such as a mirror, that is oriented (e.g., at a 45° angle) to direct light L emitted by the light source 50 to the light detector 52. In another embodiment, the reflector is provided as a prismatic reflector 80 (FIGS. 7, 14, and 15), which is formed of a light-transmissive material (e.g., a clear plastic material) and has inner and outer walls 82 and 84 and first and second end walls 86 and 88 (FIG. 14). The inner wall 82 is positioned against the inner side wall portion 58 of the centrifugal separation chamber 32 and is oriented substantially perpendicular to the initial path of the light L from the light source 50. This allows light L from the light source 50 to enter into the prismatic reflector 80 via the inner wall 82 while continuing along its initial path. The light L continues through the prismatic reflector 80 along its initial path until it encounters the first end wall 86. The first end wall 86 is oriented at an angle (e.g., an approximately 45° angle) with respect to the inner wall 82 and the second end wall 88, causing the light L to be redirected within the prismatic reflector 80, rather than exiting the prismatic reflector 80 via the first end wall 86.

The first end wall 86 directs the light L at an angle to its initial path (which may be an approximately 90° angle, directing it from a path toward the rotational axis 38 to a path that is generally parallel to the rotational axis 38) toward the second end wall 88 (FIG. 15). The first end wall 86 and the inner and outer walls 82 and 84 of the prismatic reflector 80 may be configured to transmit the redirected light L from the first end wall 86 to the second end wall 88 by total internal reflection. The second end wall 88 is oriented substantially perpendicular to the redirected path of the light L through the prismatic reflector 80, such that the light L will exit the prismatic reflector 80 via the second end wall 88, continuing along its redirected path. In one embodiment, the second end wall 88 is roughened or textured or otherwise treated or conditioned to diffuse the light L as it exits the prismatic reflector 80, which may better ensure that the light L reaches the light detector 52 (FIG. 7).

Figure 16:
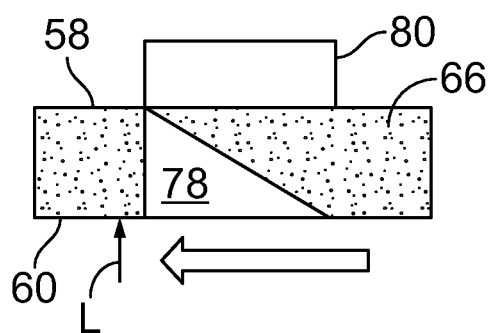
FIGS. 16-19 are diagrammatic views of the ramp and prismatic reflector of the centrifugal separation chamber passing through the path of light from the light source during a calibration phase.
Figure 20:
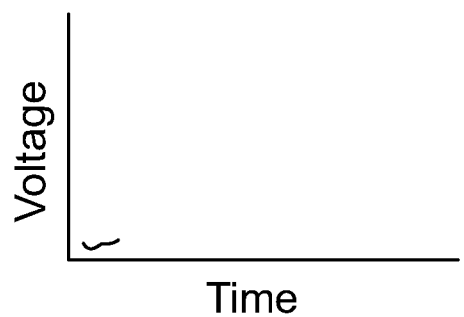
FIGS. 20-23 are diagrammatic views of the voltage output or signal transmitted by the light detector during the conditions shown in FIGS. 16-19, respectively.
Figure 17:
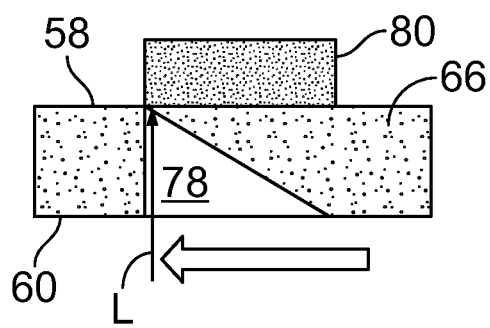

The prismatic reflector 80 may be angularly aligned with the ramp 78, such that the light L from the light source 50 will only enter into the prismatic reflector 80 when the ramp 78 has been rotated into the path of the light L. At all other times (when the ramp 78 is not in the path of the light L), the light L will not reach the prismatic reflector 80 and, thus, will not reach the light detector 52. This is illustrated in FIGS. 16-19, which show the ramp 78 and prismatic reflector 80 as the centrifugal separation chamber 32 is rotated about the rotational axis 38. In FIG. 16, the ramp 78 and prismatic reflector 80 have not yet been rotated into the initial path of the light L from the light source 50. At this time, no light is transmitted to the light detector 52, such that the output voltage of the light detector 52 (i.e., the signal transmitted from the light detector 52 to the controller 18) is in a low- or zero-state (FIG. 20).

Figure 21:
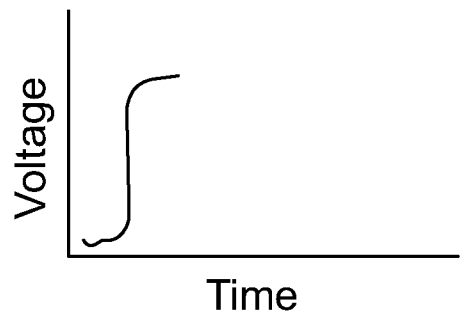

Upon the ramp 78 first being rotated into the initial path of the light L from the light source 50 (FIG. 17), the light L will begin to reach the prismatic reflector 80, which directs the light L to the light detector 52. This causes the voltage output of the light detector 52 (i.e., the signal transmitted from the light detector 52 to the controller 18) to increase to a non-zero value or state, as shown in FIG. 21.

Figure 18:
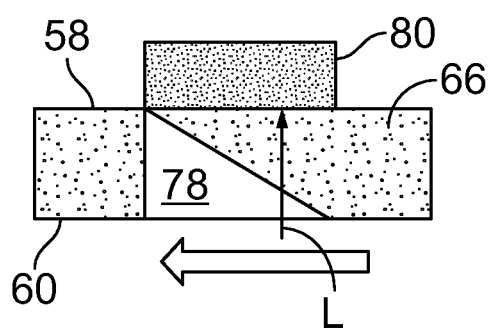
Figure 22:
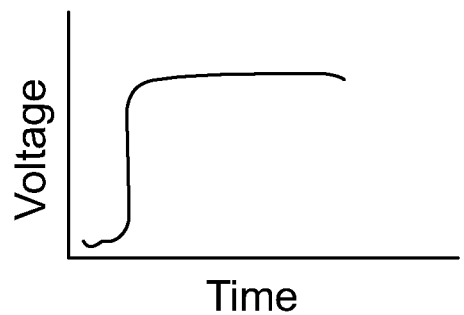
Figure 19:
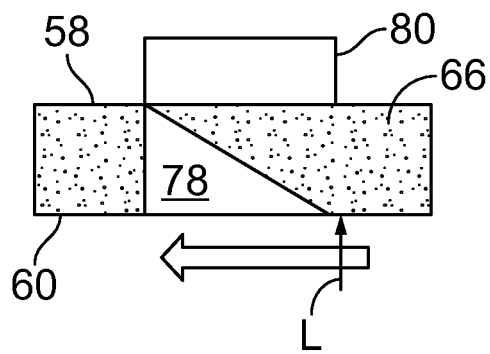

During a calibration phase, the channel 66 is filled with a fluid that will transmit the light L rather than absorbing or reflecting the light or otherwise preventing the light L from reaching the prismatic reflector 80, such that the voltage output of the light detector 52 will remain generally constant as the ramp 78 and prismatic reflector 80 are rotated through the initial path of the light L from the light source 50 (FIGS. 18 and 22). Such a calibration phase may coincide with a priming phase during which saline is pumped through the fluid flow circuit 12 to prime the fluid flow circuit 12 or may comprise a separate phase. A calibration phase may be useful in ensuring the proper operation of the light source 50 and the light detector 52, standardizing the readings taken during a separation procedure in case of any irregularities or imperfections of the centrifugal separation chamber 36, and establishing a baseline value for the signal transmitted from the light detector 52 to the controller 18 when the ramp 78 and prismatic reflector 80 are aligned with the light source 50. During a fluid separation procedure, the voltage output of the light detector 52 will typically not remain constant as the ramp 78 and prismatic reflector 80 are rotated through the initial path of the light L from the light source 50 because the different fluid layers displayed on the ramp 78 will allow different amounts of light L to reach the prismatic reflector 80.

Figure 23:
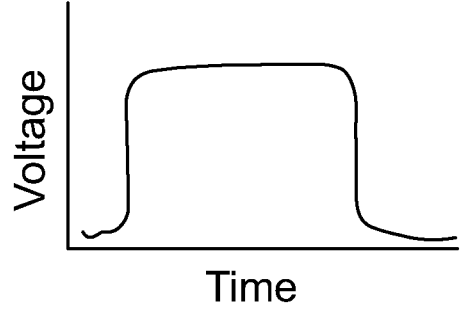

The ramp 78 and prismatic reflector 80 are eventually rotated out of alignment with the light source 50 (FIG. 19), at which time no light L will reach the prismatic reflector 108 and the voltage output of the light detector 52 will return to its low- or zero-state (FIG. 23).

During the time that the ramp 78 and prismatic reflector 80 are rotated through the path of the light L from the light source 50, the light L continues through the channel 66 and the fluids in the channel 66. At least a portion of the light L (i.e., the portion not absorbed or reflected by the fluids) exits the channel 66 by striking and entering a light-transmissive portion of the inner side wall portion 58. The light L passes through the inner side wall portion 58 and enters the prismatic reflector 80, which redirects the light L from its initial path to the light detector 52, as described above.

The light detector 52 generates a signal that is transmitted to the interface control module of the controller 18, which can determine the location of the interface N on the ramp 78. In one embodiment, the location of the interface N is associated with a change in the amount of light L that is transmitted through the less optically dense layer P and the optically dense layer R. For example, the light source 50 may be configured to emit a light L that is more readily transmitted by platelet-rich plasma or platelet-poor plasma than by red blood cells, such as red visible light (from a laser or a differently configured light source L), which is substantially absorbed by red blood cells. The less optically dense layer P and the optically dense layer R each occupy a certain portion of the ramp 78, with the light detector 52 receiving different amounts of light L depending on whether the light L travels through the less optically dense layer P on the ramp 78 or the optically dense layer R on the ramp 78. The percentage of the ramp 78 occupied by each layer is related to the location of the interface N in the channel 66. Thus, by measuring the amount of time that the voltage output or signal from the light detector 52 is relatively high (corresponding to the time during which the light L is passing through only the less optically dense layer P on the ramp 78), the controller 18 may determine the location of the interface N and take steps to correct the location of the interface N, if necessary. An exemplary approach to adjustment of the position of the interface N is described in greater detail in PCT Patent Application Publication No. WO 2018/053217 A1.

2. Adjustment of Light Source of Detection Assembly

Figure 24:
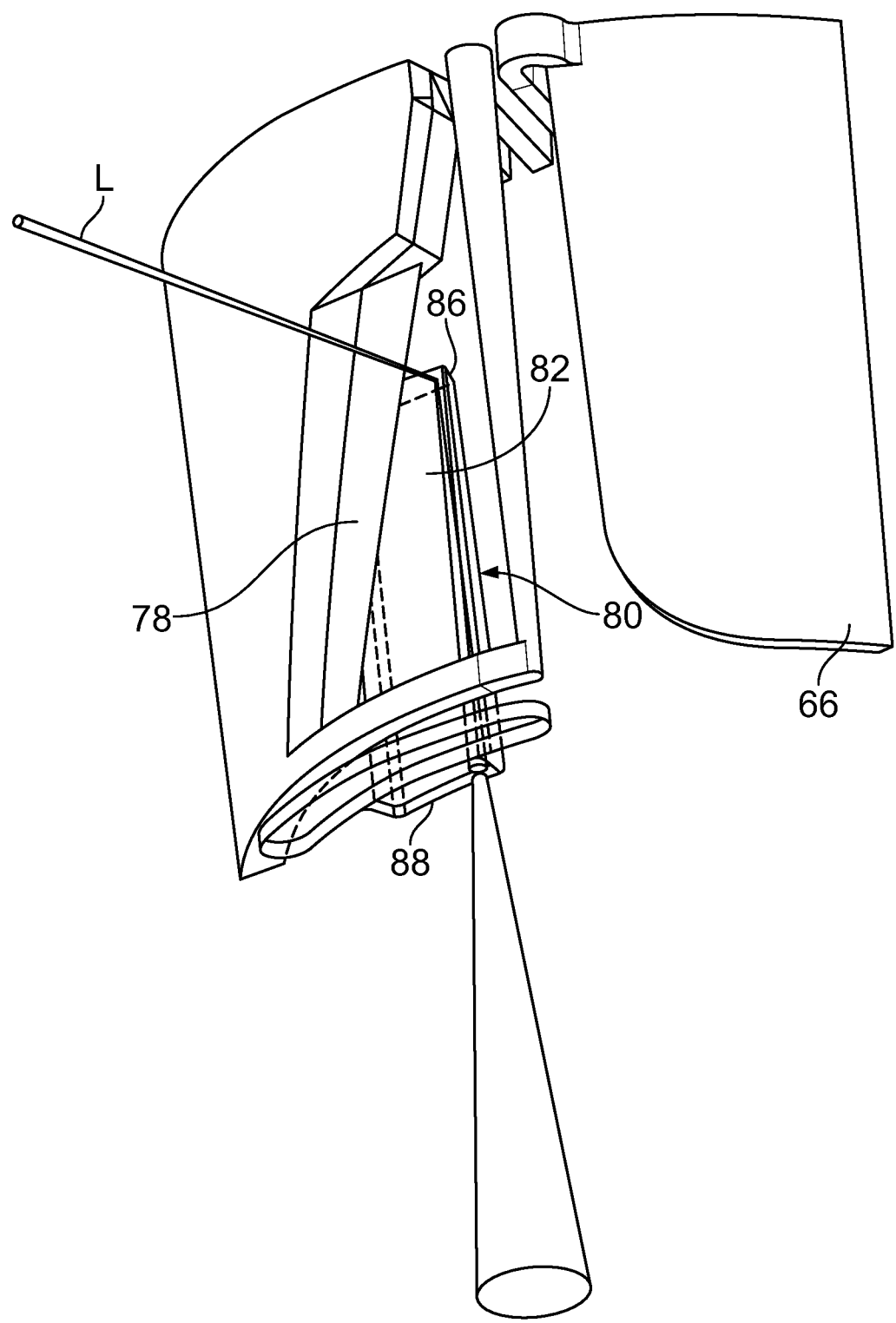
FIG. 24 is a perspective view of the channel and prismatic reflector of the of the centrifugal separation chamber of FIGS. 8-10, with the prismatic reflector in proper alignment with the light source of the interface monitoring assembly.
Figure 25:
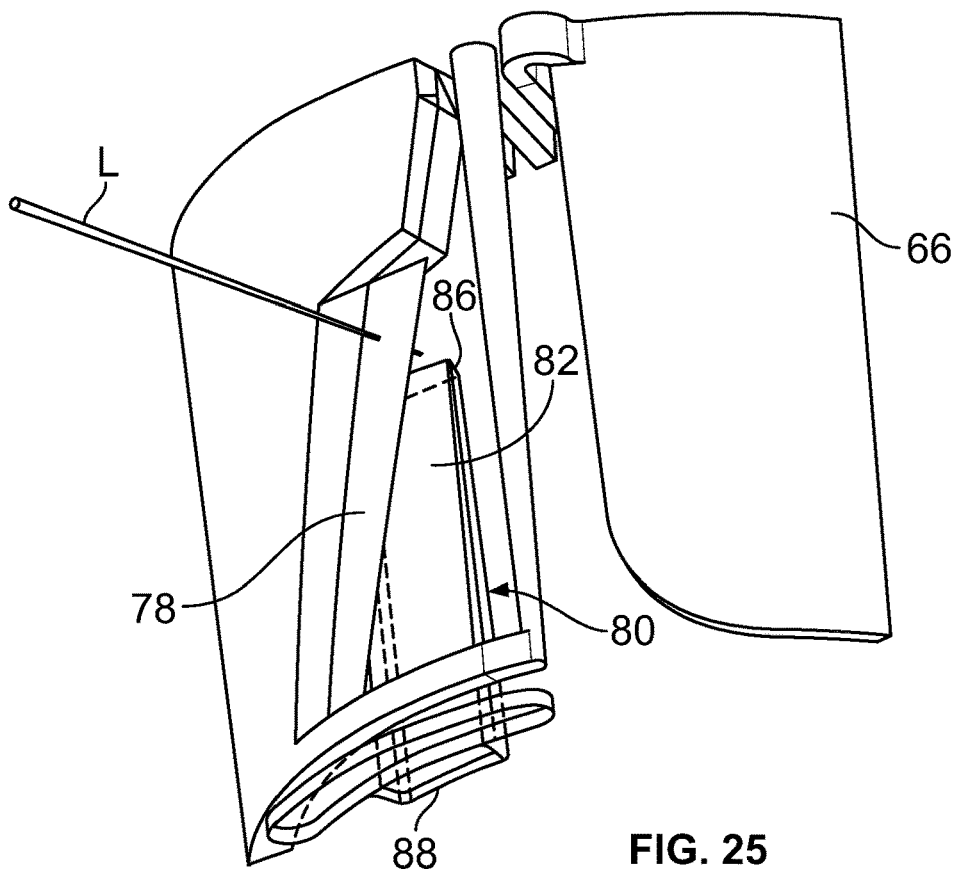
FIGS. 25 and 26 are perspective views of the channel and prismatic reflector of the of the centrifugal separation chamber of FIGS. 8-10, with the prismatic reflector not in proper alignment with the light source of the interface monitoring assembly.
Figure 26:
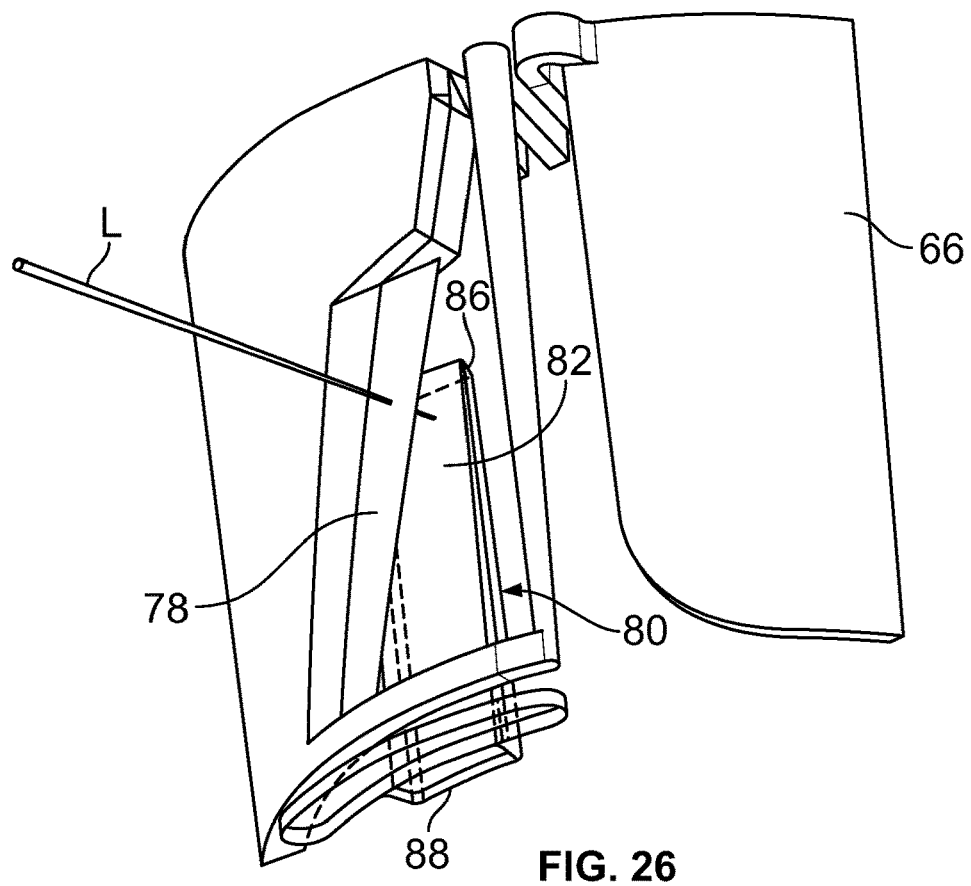

It will be appreciated that light L from the light source 50 must reach the light detector 52 to determine (and adjust) the location of the interface N. For example, FIG. 24 shows the light source 50 in a proper position with respect to the first end wall 86 of the prismatic reflector 80, allowing the light L from the light source 50 to be transmitted through the prismatic reflector 80 for receipt by the light detector 52. On the other hand, FIGS. 25 and 26 show the light source 50 out of alignment with the first end wall 86 of the prismatic reflector 80, which prevents the light L from reaching the light detector 52. In the orientation of FIG. 25, the light source 50 is positioned too high with respect to the first end wall 86, such that the light L does not strike any portion of the prismatic reflector 80. In the orientation of FIG. 26, the light source 50 is positioned too low with respect to the first end wall 86, such that the light L will enter the prismatic reflector 80 via the inner wall 82 of the prismatic reflector 80, but at a position that will not cause the light L to strike the first end wall 86.

For a light source 50 that is not movable, the default position of the light source 50 assumes a particular orientation and position of the prismatic reflector 80, which depends upon the proper installation and orientation of the centrifugal separation chamber 32 into the centrifuge compartment 34. Thus, if the centrifugal separation chamber 32 is not properly installed and oriented, the prismatic reflector 80 may not be capable of properly directing light L from the light source 50 to the light detector 52. Even if the centrifugal separation chamber 32 is properly installed and oriented, it may be the case that the prismatic reflector 80 is not ideally positioned and/or oriented to direct light L from the light source 50 to the light detector 52 (e.g., due to tolerance stack-ups and/or an imperfection in the configuration of the centrifugal separation chamber 32).

Figure 27:
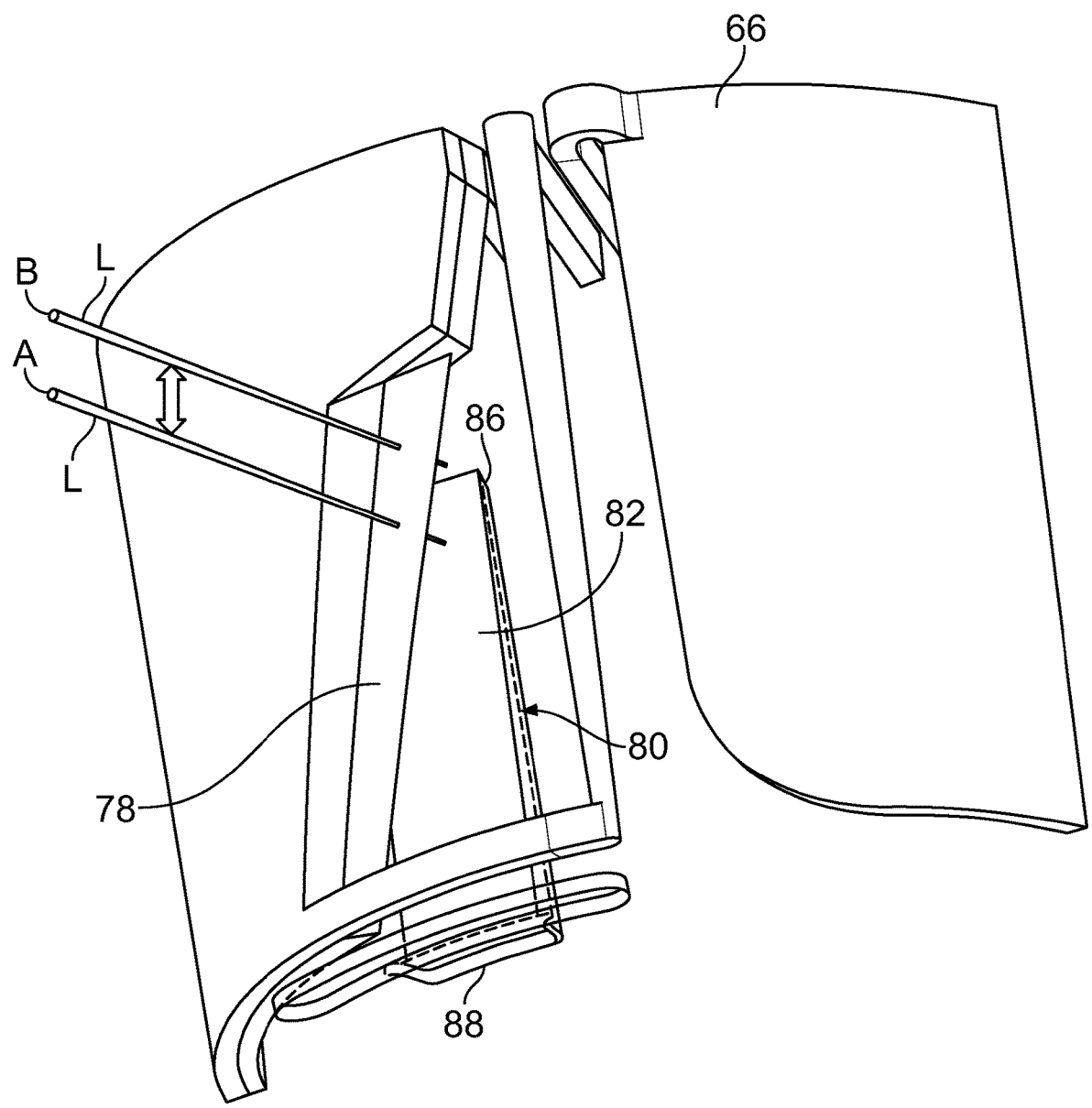
FIG. 27 is a perspective view of the channel and prismatic reflector of the of the centrifugal separation chamber of FIGS. 8-10, showing an exemplary range of movement of the light source of the interface monitoring assembly.

According to an aspect of the present disclosure, the interface monitoring assembly includes an adjustment system associated with the light source 50 and configured to adjust the position of the light source 50 with respect to the stationary surface of the centrifuge compartment 34 with which the light source 50 is associated. In the case of the light source 50 of the interface monitoring system, the position of the light source 50 is adjustable in a direction parallel to the rotational axis 38, with FIG. 27 showing an exemplary range of movement of the light source 50. FIG. 27 shows the two extreme positions "A" and "B" of the light source 50, with A representing the lowest position into which the light source 50 may be moved by the adjustment system and B representing the highest position into which the light source 50 may be moved by the adjustment system. It may be advantageous for the extreme positions A and B to be selected as positions in which the light source 50 will be out of alignment with the first end wall 86 of the prismatic reflector 80. As will be explained in greater detail, by such a configuration, the controller 18 (or a separate controller associated with the adjustment system) may be capable of determining the location of the upper and lower edges of the first end wall 86 by controlling the adjustment system to move the light source 50 from one extreme position A, B to the other extreme position A, B. However, it should be understood that the adjustment system may be capable of any range of movement of the light source 50 without departing from the scope of the present disclosure.

Figure 28:
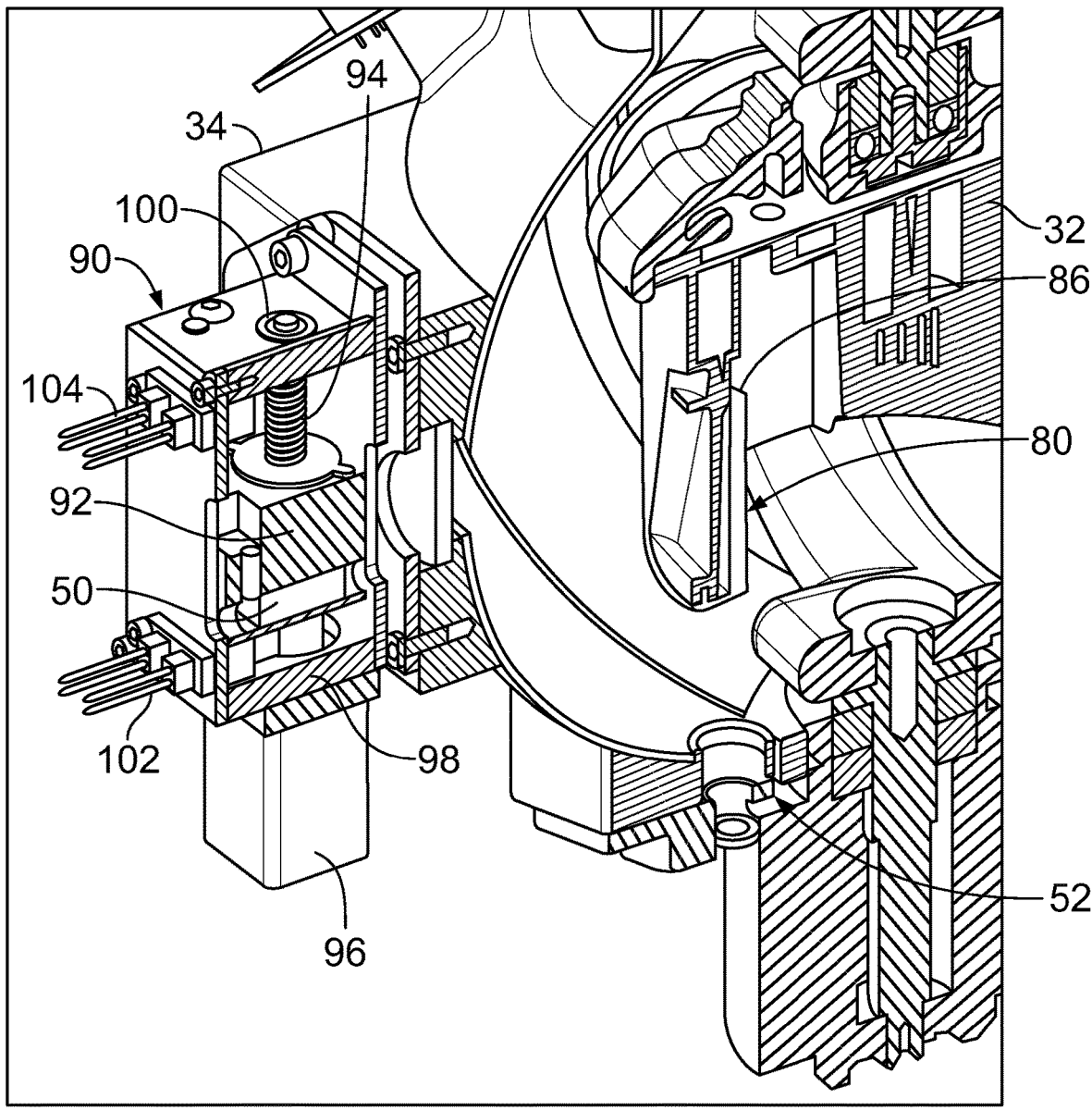
FIG. 28 is a perspective view of an exemplary adjustment system for adjusting the position of the light source of the interface monitoring assembly, with selected portions broken away for illustrative purposes.

The adjustment system may be variously configured without departing from the scope of the present disclosure, but in the illustrated embodiment of FIG. 28, the adjustment system 90 includes a carriage 92 receiving at least a portion of the light source 50, a lead screw 94 associated with the carriage 92, and a stepper motor 96. The illustrated adjustment system 90 further includes a housing 98 secured to a stationary surface of the centrifuge compartment 34 and defining an interior space in which the carriage 92 and at least a portion of the lead screw 94 are positioned. The stepper motor 96 is shown as being secured to a bottom end of the housing 98, positioned at least partially outside of the housing 98, but it should be understood that the stepper motor 96 may be positioned inside the housing 98 without departing from the scope of the present disclosure. However, positioning the stepper motor 96 inside the housing 98 may limit the range of movement of the carriage 92, such that it may be preferable to position the stepper motor 96 at least partially outside of the housing 98.

The stepper motor 96 is operatively associated with the lead screw 94, such that actuation of the stepper motor 96 (by the controller 18 or a separate controller associated with the adjustment system 90) will rotate the lead screw 94. In the illustrated embodiment, a lower end of the lead screw 94 (not visible) is associated with the stepper motor 96, while an upper end of the lead screw 94 is rotatably received by a bearing 100 incorporated into the upper end of the housing 98. The lead screw 94 is configured such that actuation of the stepper motor 96 will cause the lead screw 94 to rotate about its central axis without translational movement with respect to the housing 98. The stepper motor 96 is reversible, with actuation of the stepper motor 96 in one direction (which may be referred to herein as a forward direction) causing rotation of the lead screw 94 in a first direction, while actuation of the stepper motor 96 in an opposite direction (which may be referred to as a reverse direction) will cause rotation of the lead screw 94 in a second direction that is opposite to the first direction.

The lead screw 94 is associated with the carriage 92 in a way that translates rotation of the lead screw 94 into movement of the carriage 92 along the lead screw 94, without rotation of the carriage 92 as it moves along the lead screw 94. Rotation of the lead screw 94 by the stepper motor 96 in one direction will cause the carriage 92 (and, hence, the light source 50) to move in one direction along the lead screw 94 (e.g., upwardly), while rotation of the lead screw 94 by the stepper motor 96 in the opposite direction will cause the carriage 92 (and, hence, the light source 50) to move in the opposite direction (e.g., downwardly). The orientation and configuration of the lead screw 94 define the range of movement of the carriage 92 and the light source 50. In the illustrated embodiment, the elongated lead screw 94 extends in a direction parallel to the rotational axis 38, thus restricting the carriage 92 and light source 50 to movement in a direction parallel to the rotational axis 38.

Figure 29:
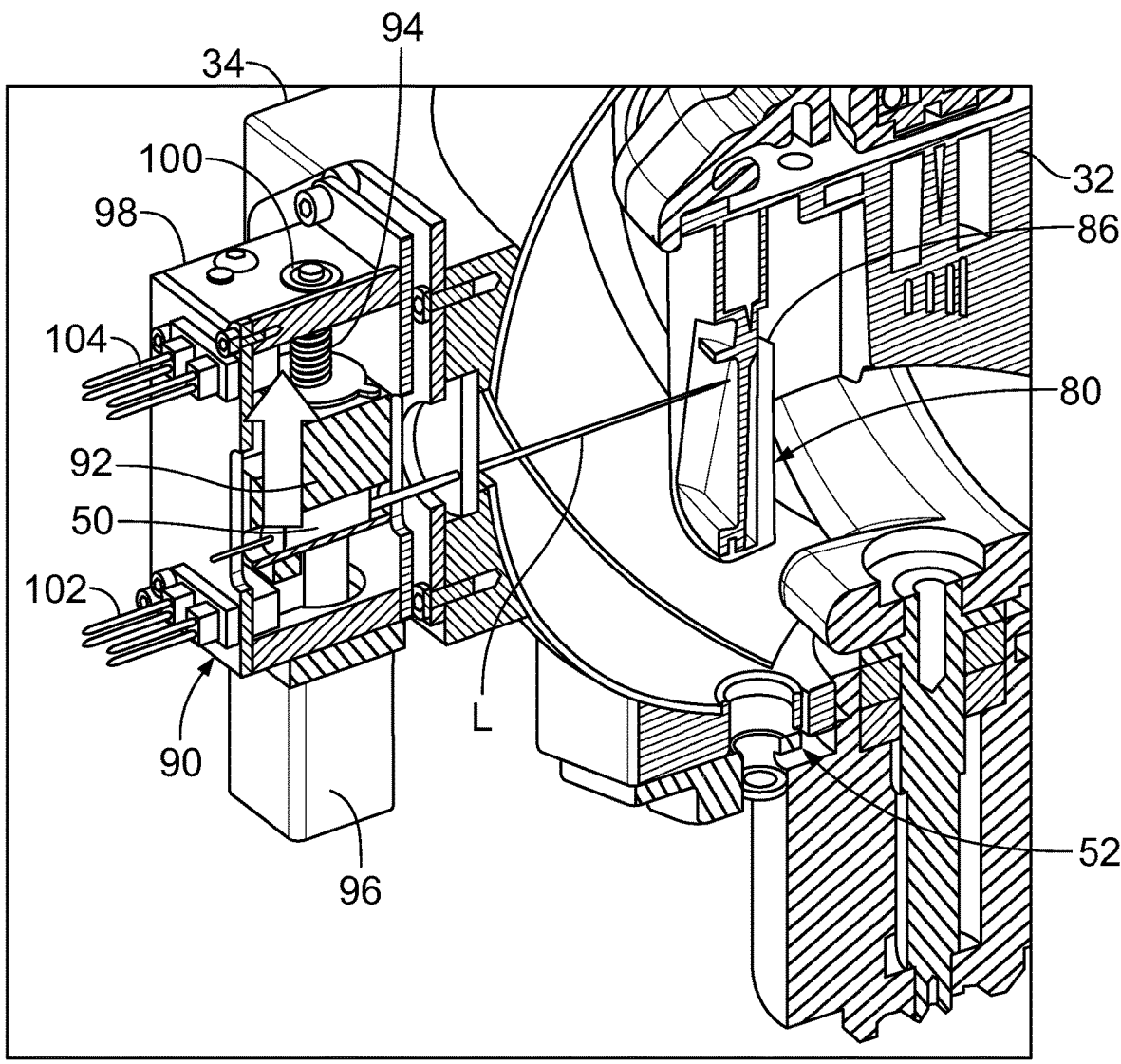
FIGS. 29-31 are perspective views of the adjustment system of FIG. 28, showing the light source in different positions.
Figure 30:
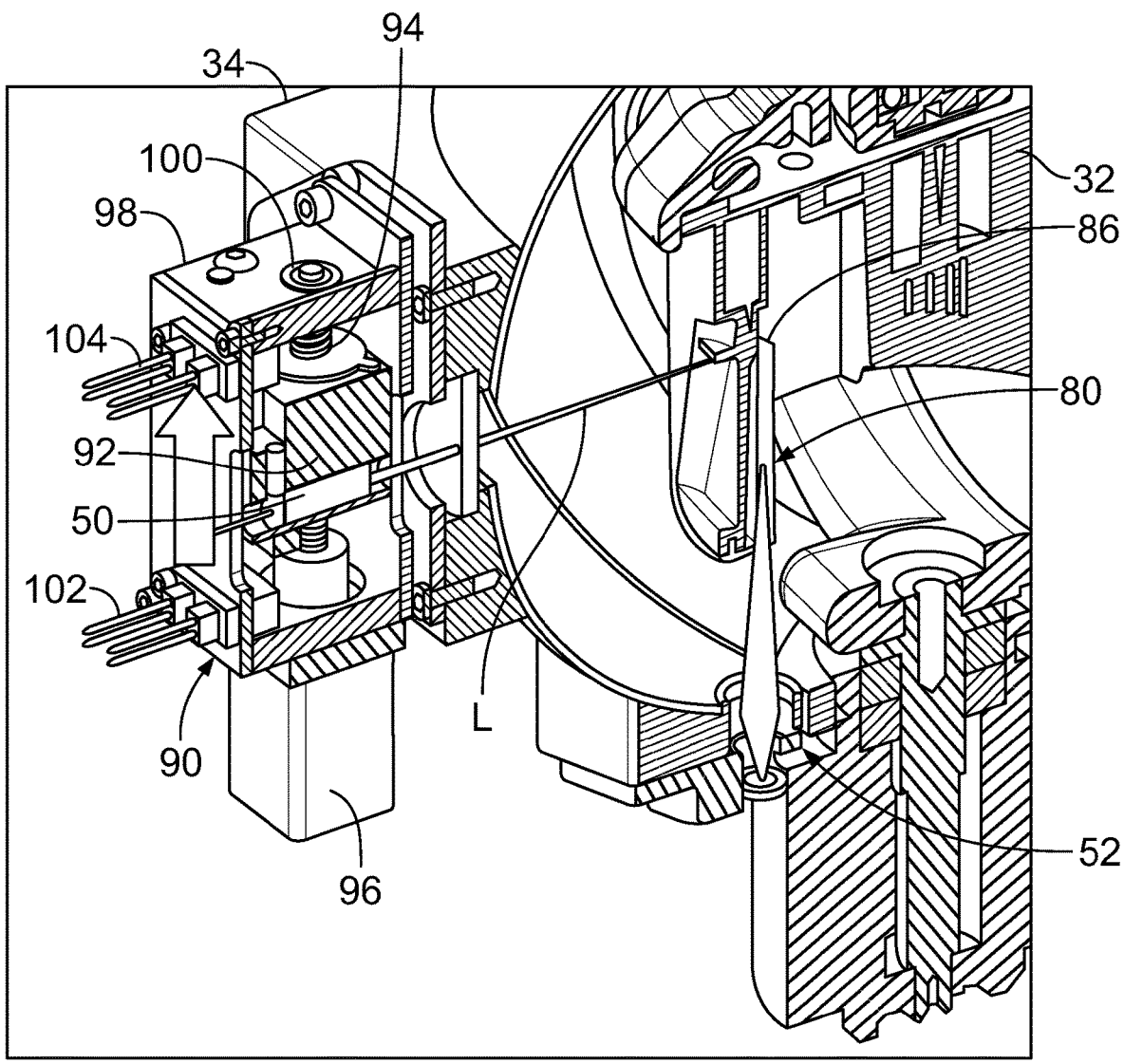
Figure 31:
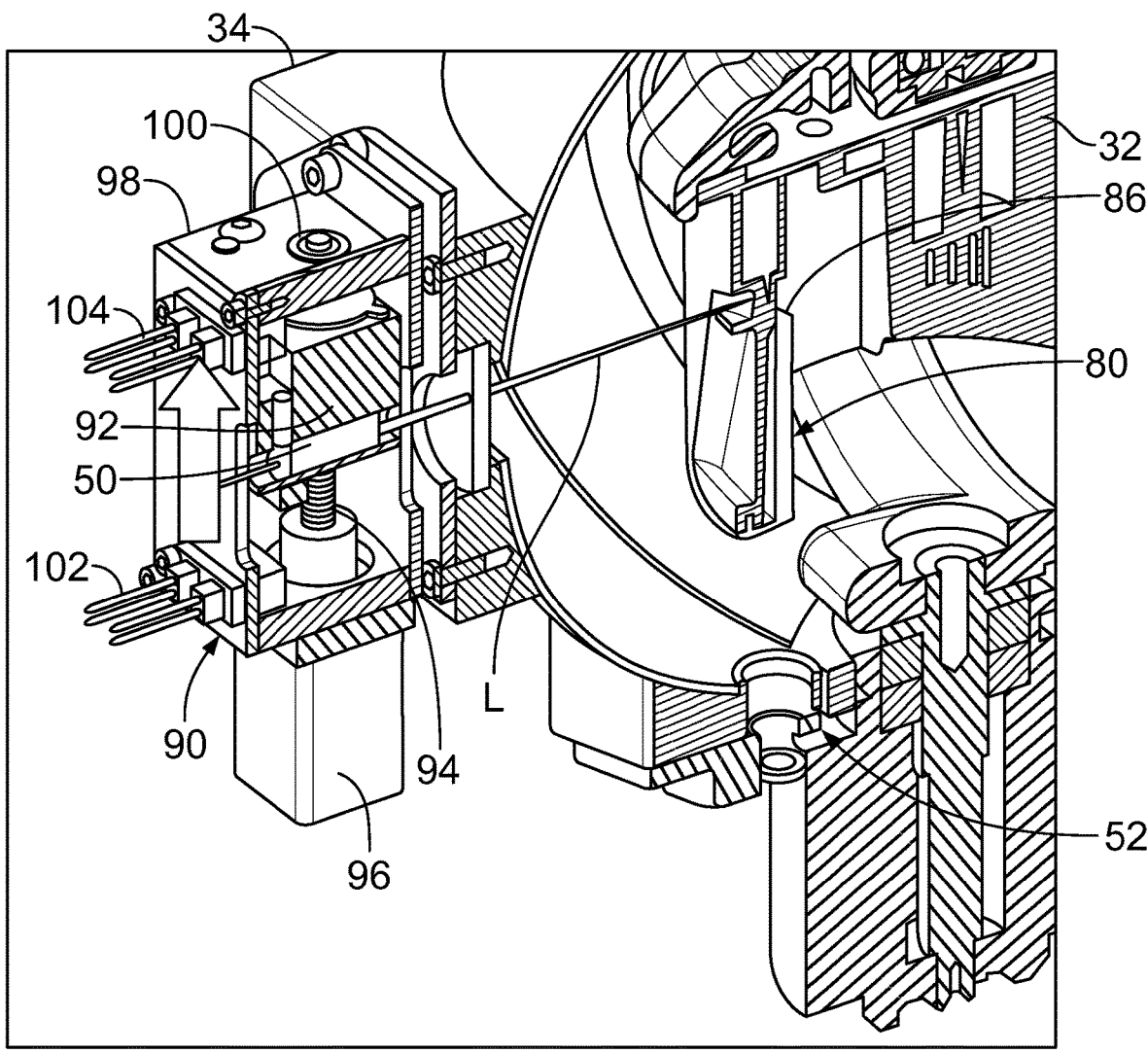

FIGS. 29-31 illustrate rotation of the lead screw 94 in one direction, which causes the carriage 92 to move in a direction from an exemplary initial position (FIG. 29) toward an intermediate position (FIG. 30) and toward an exemplary final position (FIG. 31). Rotation of the lead screw 94 in the opposite direction will cause the carriage 92 to move in a direction from the final position (FIG. 31) toward the initial position (FIG. 29). The initial position may correspond to one of the extreme positions A of FIG. 27, while the final position corresponds to the other extreme position B of FIG. 27. FIGS. 29 and 31 show the initial position of the carriage 92 and light source 50 as being a lowest position, with the final position being a highest position, but it should be understood that the initial position may instead be the highest position (FIG. 31), while the final position is the lowest position (FIG. 29). In either case, the light source 50 may be positioned out of alignment with the first end wall 86 of the prismatic reflector 80 in the initial and final positions of FIGS. 29 and 31 (as described above), while being in alignment with the first end wall 86 in the intermediate position of FIG. 30.

The adjustment system 90 may include additional components without departing from the scope of the present disclosure. For example, the adjustment system 90 may further include a home sensor 102 associated with the controller 18 (or some other controller associated with the adjustment system 90) and configured to determine when the carriage 92 is in an initial or home position. A second sensor 104 may be provided to determine when the carriage 92 is in some other position (e.g., a final position).

It should be understood that the illustrated adjustment system 90 is merely exemplary and that adjustment systems for adjusting the position of the light source of a detection assembly may be differently configured without departing from the scope of the present disclosure. For example, while the combination of a stepper motor 96 and lead screw 94 may be advantageous (on account of the ability to precisely control the operation of the stepper motor 96 and determine how many steps have been taken, which is indicative of the position of the light source 50), it is within the scope of the present disclosure to employ some other mechanism for adjusting the position of the light source. For example, alternative mechanisms include (without limitation): pneumatic or hydraulic cylinders, a piezoelectric actuator, a cam actuator, a telescoping linear actuator, and a magnetic linear motor, with a possible preference of a mechanism that allows for tracking of the position of the light source.

Regardless of the particular configuration of the adjustment system and the associated light source, the adjustment system may be controlled to execute one or more routines to determine an optimized or at least acceptable position for the light source (which position is referred to herein as a "monitoring" position). As the alignment and configuration of a monitored component will not tend to change during a procedure, it may be sufficient for adjustment of the position of the light source to be carried out once. In one embodiment, the position of the light source is calibrated during the priming phase in which saline is pumped through the fluid flow circuit 12 to prime the fluid flow circuit 12. This may be preferred to adjustment of the light source during active processing, as various factors (e.g., the nature of the fluid being separated during a fluid separation procedure) may make it more difficult to assess the alignment of the light source. However, it should be understood that adjustment systems according to the present disclosure may be used to move the light source of a detection assembly at any time, including repositioning the light source multiple times during a single procedure.

Figure 32:
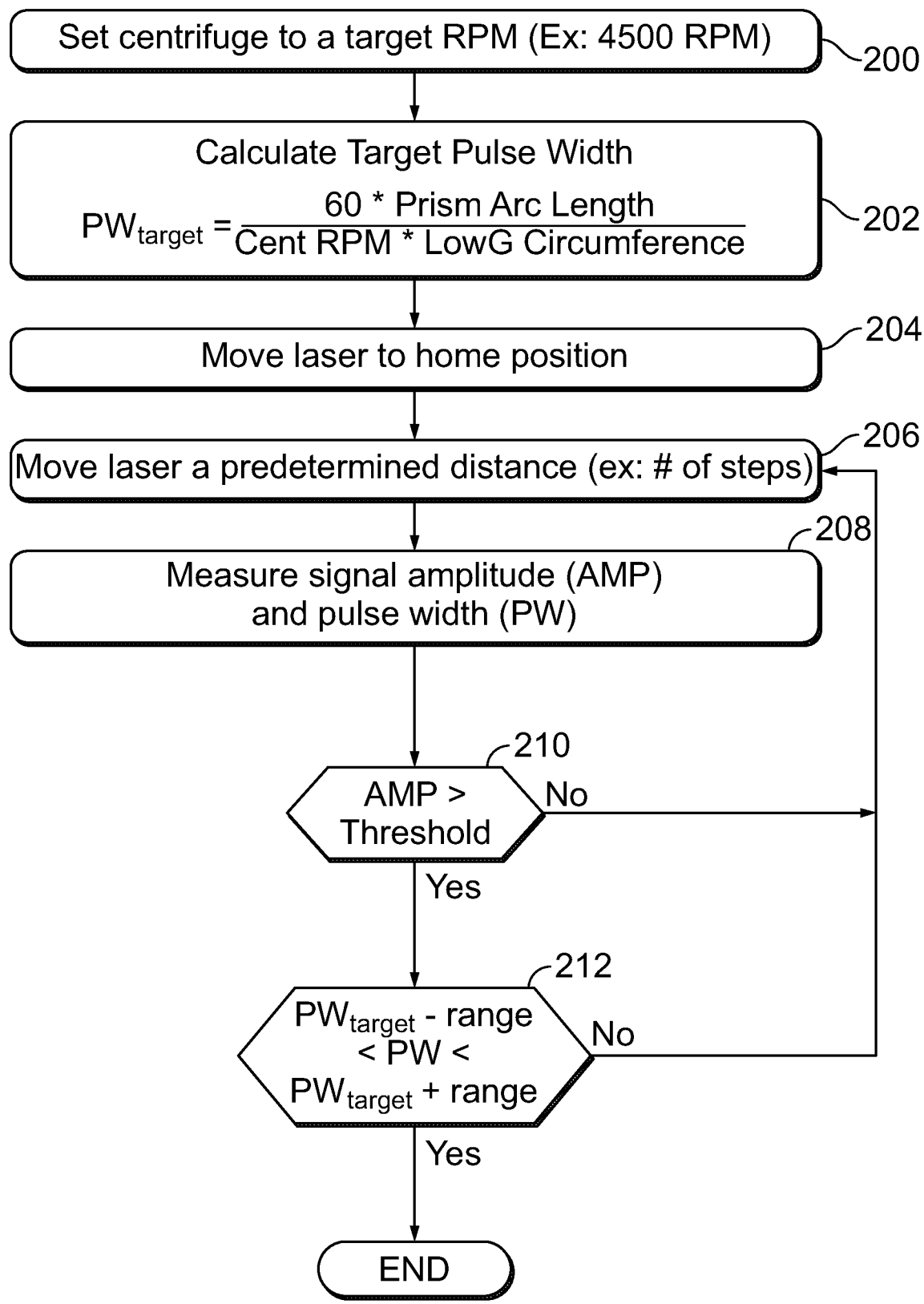
FIGS. 32-34 are flowcharts of exemplary approaches to adjusting the position of the light source of a detection assembly according to an aspect of the present disclosure.
Figure 33:
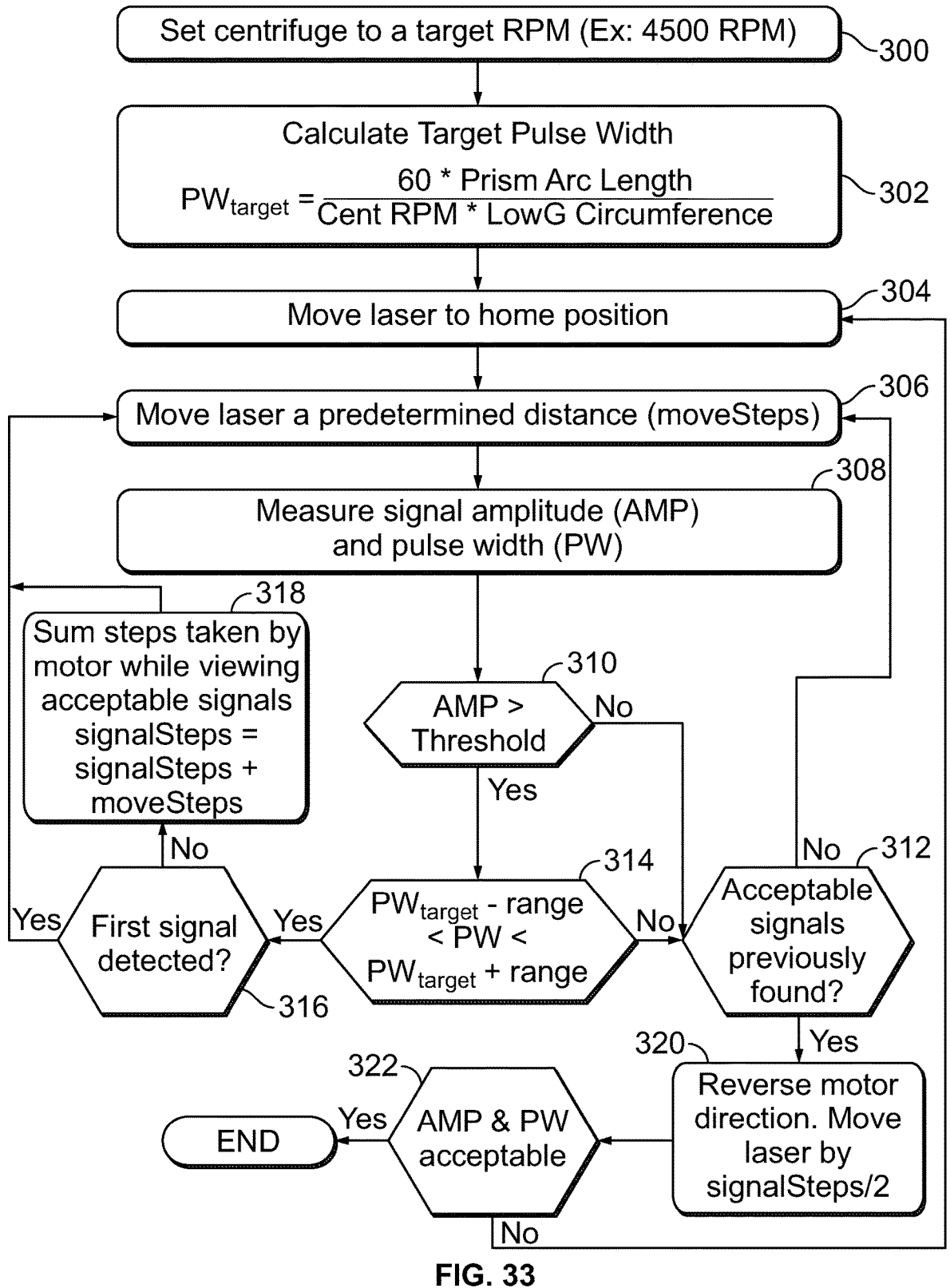
Figure 34:
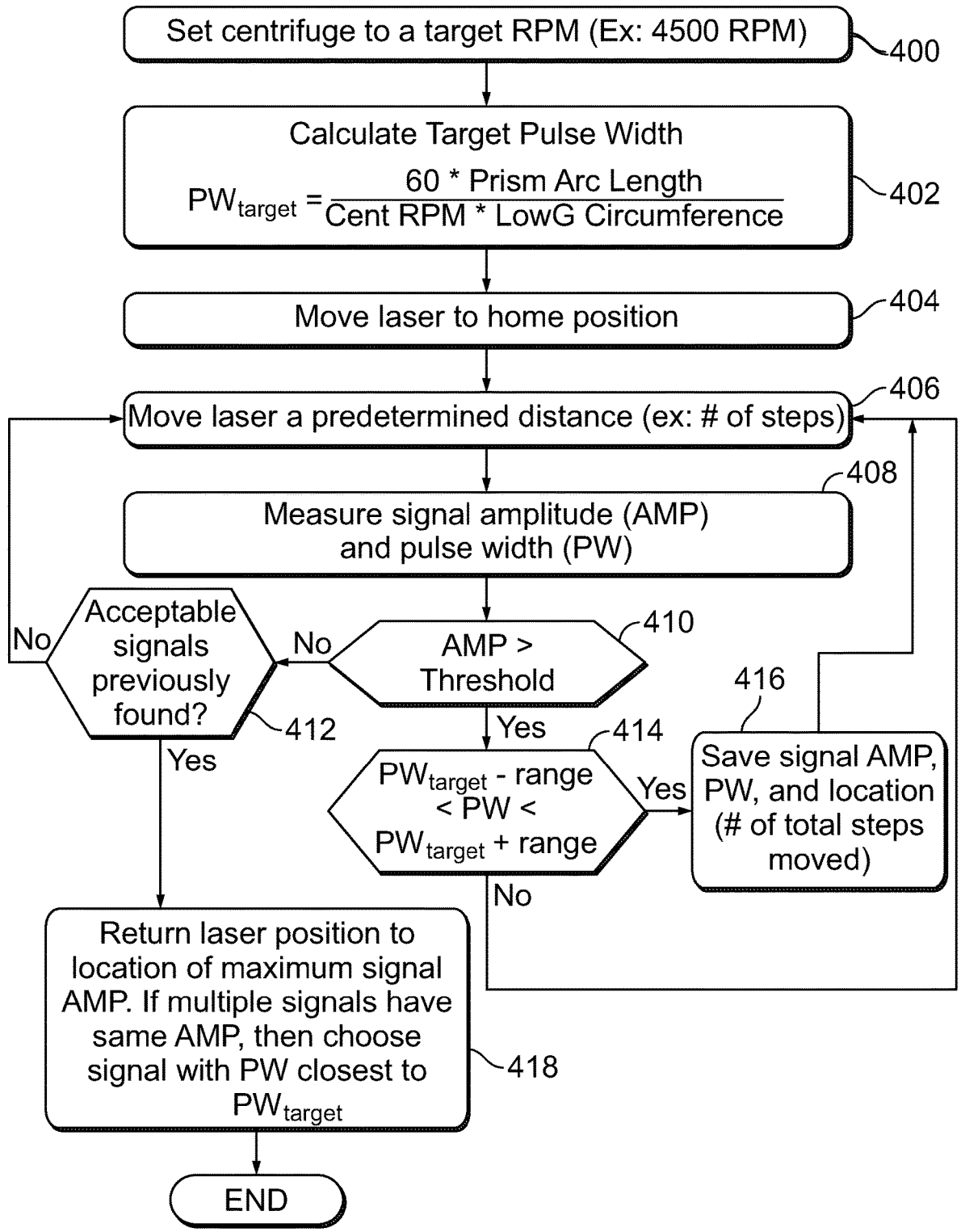

FIGS. 32-34 illustrate three possible approaches to determining a monitoring position for the light source 50 of an interface monitoring assembly. It should be understood that these approaches are merely exemplary and that other approaches may be employed without departing from the scope of the present disclosure. Additionally, it should be understood that, while these routines are presented in the context of adjustment of the position of the light source 50 of an interface monitoring assembly, the principles illustrated by these routines may be employed in adjusting the position of the light source of a differently configured detection assembly.

In the routine of FIG. 32, the centrifugal separation chamber 32 is rotated about the rotational axis 38, as indicated at 200 in FIG. 32. The rotational speed of the centrifugal separation chamber 32 may vary without departing from the scope of the present disclosure, with the rotational speed being the speed at which the centrifugal separation chamber 32 is rotated to separate blood during active processing (which may be approximately 4,500 rpm) in one embodiment.

A target or expected pulse width is calculated based on the rotational speed of the centrifugal separation chamber 32, as indicated at 202 in FIG. 32. In the illustrated embodiment, the target pulse width ($PW_{target}$) is calculated using the following equation:

$$PW_{target} = \frac{60 * \text{Prism Arc Length}}{\text{Cent RPM} * \text{LowG Circumference}}, \quad (1)$$

in which:

Prism Arc Length is the arc length of the prismatic reflector 80 about the rotational axis 32, Cent RPM is the rotational speed of the centrifugal separation chamber 32, and LowG Circumference is the circumference of the low-g side wall portion 58 of the centrifugal separation chamber 32.

$PW_{target}$ corresponds to the pulse width of the signal transmitted from the light detector 52 shown in FIG. 23, which represents a full-strength signal being transmitted by the light detector 52 across the entire arc length of the prismatic reflector 80 during one rotation of the centrifugal separation chamber 32. As explained above, the light detector 52 will only transmit an elevated signal when the prismatic reflector 80 is rotating through the path of the light L emitted by the light source 50 and not when the prismatic reflector 80 is out of alignment with the light L.

Next, the light source 50 is moved to its home or initial position, as indicated at 204 in FIG. 32. In the case of an adjustment system 90 employing a stepper motor 96 and one or more sensors 102, 104, the light source 50 is moved until it is determined to be in its initial position, followed by the position step counter being set to zero (i.e., "home"). In an alternative embodiment, the adjustment system 90 may instead be commanded to return the light source 50 to its home or initial position at the end of each procedure, rather than during this calibration phase.

With the light source 50 in its initial position, the adjustment system 90 is commanded to move the light source 50 a predetermined distance (e.g., a predetermined number of steps in the case of an adjustment system 90 employing a stepper motor 96), as indicated at 206 in FIG. 32. In the illustrated embodiment, the signal from the light detector 52 is not analyzed when the light source 50 is in its initial position because the initial position has been selected so as to place the light source 50 out of alignment with the first end wall 86 of the prismatic reflector 80 (i.e., at a "non-monitoring" position). However, in embodiments in which the initial position is selected such that the light source 50 may be aligned with the first end wall 86 of the prismatic reflector 80 (i.e., in a potential monitoring position), the signal from the light detector 52 when the light source 50 is in its initial position may be analyzed.

In either case, the signal from the light detector 52 (if any) is analyzed to determine its amplitude (AMP) and pulse width (PW), as indicated at 208 in FIG. 32. The amplitude is compared to a minimum amplitude or threshold value (Threshold), as indicated at 210 in FIG. 32. Threshold is selected to determine whether the signal from the light detector 52 is a high-intensity signal and, as such, may vary in magnitude from device to device. In one embodiment, Threshold is selected to be a percentage of the amplitude of the full-strength signal shown in FIG. 23 (e.g., with Threshold being equal to the amplitude of a signal that is 80% or 85% or 90% of the amplitude of a full-strength signal, which may be experimentally determined and specific to the device).

When the amplitude of the signal from the light detector 52 is less than the minimum amplitude or threshold value (which includes situations in which the light detector 52 transmits no signal), the adjustment system 90 is commanded to move the light source 50 to another location (indicated in FIG. 32 as an arrow from 210 to 206) that is farther from the initial position than the position of the light source 50 when the previous signal was analyzed. The signal from the light detector 52 (if any) with the light source 50 in the new position is then analyzed to determine its amplitude and pulse width (as at 208), with the amplitude of the new signal being compared to the minimum amplitude or threshold value (as at 210). This process is repeated until the light source 50 is at a position in which the signal from the light detector 52 has an amplitude that is at least equal to the minimum amplitude or threshold value.

When the amplitude of the signal from the light detector 52 is at least equal to the minimum amplitude or threshold value, the pulse width of the signal is compared to the target pulse width, as indicated at 212 in FIG. 32. In the illustrated embodiment, the signal is analyzed to determine whether its pulse width is sufficiently close or at least substantially equal to the target pulse width. This comparison is represented in FIG. 32 by the following equation:

$$PW_{target} - \text{range} < PW < PW_{target} + \text{range} \quad (2),$$

in which range is an allowed difference between the target pulse width and the measured pulse width. The magnitude of range may vary without departing from the scope of the present disclosure, with range being 20 µs in one embodiment. It should be understood that FIG. 32 illustrates an exemplary approach to comparing a measured pulse width to a target pulse width. For example, in another embodiment, different upper and lower range values may be employed. In yet another embodiment, the measured pulse width may be required to be equal to the target or expected pulse width.

If the measured pulse width satisfies Equation 2, it is considered to be sufficiently close or at least substantially equal to the target pulse width. Otherwise, if the measured pulse width does not satisfy Equation 2, the adjustment system 90 is commanded to move the light source 50 to another location (indicated in FIG. 32 as an arrow from 212 to 206) that is farther from the initial position than the position of the light source 50 when the previous signal was analyzed. The signal from the light detector 52 (if any) with the light source 50 in the new position is then analyzed to determine its amplitude and pulse width (as at 208), with the amplitude of the new signal being compared to the minimum amplitude or threshold value (as at 210) and the pulse width of the new signal being compared to the target pulse width (as at 212). This process is repeated until the light source 50 is at a position in which the signal from the light detector 52 has an amplitude that is at least equal to the minimum amplitude or threshold value and a pulse width that is sufficiently close or at least substantially equal to the target pulse width.

Upon first determining that the measured pulse width of the signal is either equal to or at least substantially equal to the target or expected pulse width and that the amplitude of the signal is at least equal to the minimum amplitude, the controller 18 (or some other controller associated with the adjustment system 90) determines that the current position of the light source 50 is the monitoring position and controls the adjustment system 90 to stop moving the light source 50. The algorithm of FIG. 32, thus, finds the first acceptable monitoring position, rather than moving the light source 50 through the entire range of motion of the adjustment system 90 to find the most optimal position. This approach may be advantageous when an emphasis is placed on quickly finding an acceptable position for the light source 50.

Turning now to the routine of FIG. 33, its initial steps are the same as the routine of FIG. 32. The centrifugal separation chamber 32 is rotated about the rotational axis 38 (as indicated at 300 in FIG. 33), a target or expected pulse width is calculated using Equation 1 (as indicated at 302 in FIG. 33), and the light source 50 is moved to its home or initial position (as indicated at 304 in FIG. 33). As noted above with regard to the routine of FIG. 32, the adjustment system 90 may instead be commanded to return the light source 50 to its home or initial position at the end of each procedure, rather than during this calibration phase.

As in the routine of FIG. 32, with the light source 50 in its initial position, the adjustment system 90 is commanded to move the light source 50 a predetermined distance (as indicated at 306 in FIG. 33) and the signal from the light detector 52 (if any) is analyzed to determine its amplitude and pulse width (as indicated at 308 in FIG. 33). As described above with regard to the routine of FIG. 32, in the illustrated embodiment, the signal from the light detector 52 is not analyzed when the light source 50 is in its initial position because the initial position has been selected so as to place the light source 50 out of alignment with the first end wall 86 of the prismatic reflector 80 (i.e., at a "non-monitoring" position). However, in embodiments in which the initial position is selected such that the light source 50 may be aligned with the first end wall 86 of the prismatic reflector 80 (i.e., in a possible monitoring position), the signal from the light detector 52 when the light source 50 is in its initial position may be analyzed.

As in the routine of FIG. 32, the amplitude is compared to a minimum amplitude or threshold value, as indicated at 310 in FIG. 33. When the amplitude of the signal from the light detector 52 is less than the minimum amplitude or threshold value (which includes situations in which the light detector 52 does not transmit a signal), the controller 18 (or another controller associated with the adjustment system 90) determines whether one or more acceptable signals (as will be defined below) have been received from the light detector 52, as indicated at 312 in FIG. 33.

When the initial position of the light source 50 is selected as a non-monitoring position (e.g., one of the extreme positions A and B shown in FIG. 27), at least one (and typically more than one) measurement will take place before an acceptable signal has been received. In this case, the adjustment system 90 is commanded to move the light source 50 to another location (indicated in FIG. 33 as an arrow from 312 to 306) that is farther from the initial position than the position of the light source 50 when the previous signal was analyzed. The signal from the light detector 52 (if any) with the light source 50 in the new position is then analyzed to determine its amplitude and pulse width (as at 308), with the amplitude of the new signal being compared to the minimum amplitude or threshold value (as at 310). This process is repeated until the light source 50 is at a position in which the signal from the light detector 52 has an amplitude that is at least equal to the minimum amplitude or threshold value.

When the amplitude of the signal from the light detector 52 is at least equal to the minimum amplitude or threshold value, the pulse width of the signal is compared to the target pulse width, as indicated at 314 in FIG. 33. In the illustrated embodiment, the signal is analyzed using Equation 2 to determine whether its pulse width is sufficiently close or at least substantially equal to the target pulse width. As explained above with regard to the routine of FIG. 32, it should be understood that FIG. 33 illustrates an exemplary approach to comparing a measured pulse width to a target pulse width. In other exemplary approaches, different upper and lower range values may be employed or the measured pulse width may be required to be equal to the target or expected pulse width.

If the measured pulse width satisfies Equation 2, it is considered to be sufficiently close or at least substantially equal to the target pulse width (thus rendering the signal an "acceptable signal" for the analysis carried out in step 312 of FIG. 33). Otherwise, if the measured pulse width does not satisfy Equation 2, the controller 18 (or some other controller associated with the adjustment system 90) again determines whether one or more acceptable signals (as defined above) have been received from the light detector 52, as indicated at 312 in FIG. 33.

As explained above, when the initial position of the light source 50 is selected as a non-monitoring position, at least one (and typically more than one) measurement will take place before an acceptable signal has been received. In this case, the adjustment system 90 is commanded to move the light source 50 to another location (again, as indicated in FIG. 33 as an arrow from 312 to 306) that is farther from the initial position than the position of the light source 50 when the previous signal was analyzed. The signal from the light detector 52 (if any) with the light source 50 in the new position is then analyzed to determine its amplitude and pulse width (as at 308), with the amplitude of the new signal being compared to the minimum amplitude or threshold value (as at 310) and the pulse width of the new signal being compared to the target pulse width (as at 314). This process is repeated until the light source 50 is at a position in which the signal from the light detector 52 has an amplitude that is at least equal to the minimum amplitude or threshold value and a pulse width that is sufficiently close or at least substantially equal to the target pulse width.

Upon determining that the measured pulse width of the signal is either equal to or at least substantially equal to the target or expected pulse width and that the amplitude of the signal is at least equal to the minimum amplitude, the controller 18 (or some other controller associated with the adjustment system 90) determines whether this is the first acceptable signal that has been received from the light detector 52, as indicated at 316 in FIG. 33. If so, the current position of the light source 50 is understood to be aligned with a first or leading edge of the first end wall 86 of the prismatic reflector 80 (with the light source 50 being out of alignment with the first end wall 86 at all previous positions). In the illustrated embodiment, in which the light source 50 is moved upwardly from a low extreme position A toward a high extreme position B, the first or leading edge of the first end wall 86 will be the lower edge of the first end wall 86.

The light source 50 is then moved again (as at 306), followed by the amplitude and pulse width of the signal from the light detector 52 being analyzed (as at 308, 310, and 314). When the subsequent signal is acceptable (which is typically the case immediately after the first edge of the first end wall 86 of the prismatic reflector 80 has been identified), the controller 18 (or some other controller associated with the adjustment system 90) again determines whether this is the first acceptable signal that has been received from the light detector 52 (again, as at 316). As this is not the first acceptable signal that has been received, the controller 18 (or some other controller associated with the adjustment system 90) calculates the distance that the light source 50 has traveled while aligned with the first end wall 86 of the prismatic reflector 80 (i.e., while the light detector 52 has been transmitting acceptable signals), as indicated at 318 in FIG. 33. This may be determined using any suitable approach, which may vary depending on the nature of the adjustment system 90. In the illustrated embodiment (in which a stepper motor 96 is employed), this distance is determined using the following equation:

$$\text{signalSteps} = \text{signalSteps} + \text{moveSteps} \qquad (3),$$

in which:

signalSteps is the total of the number of steps that the stepper motor 96 has taken while the light source 50 is aligned with the first end wall 86 of the prismatic reflector 80, and moveSteps is the number of steps that the stepper motor 96 has moved since the previous signal was received.

Thus, when the analysis represented in FIG. 33 at step 318 is first performed, signalSteps will be zero and then updated (by adding moveSteps, according to Equation 3) to be equal to moveSteps. The process of moving the light source 50 (as at 306), followed by the amplitude and pulse width of the signal from the light detector 52 being analyzed (as at 308, 310, and 314) and updating signalSteps (as at 318) is repeated as long as the light detector 52 continues transmitting acceptable signals (which is indicative of the light source 50 remaining in alignment with the first end wall 86 of the prismatic reflector 80). It will be seen that, when the light source 50 is moved the same distance during each iteration of this loop, signalSteps will be equal to moveSteps multiplied by number of times that the analysis of step 318 has been performed (e.g., if moveSteps is equal to 5 steps and the analysis of step 318 has been performed seven times, then signalSteps will be equal to 35). However, it should be understood that the light source 50 is not necessarily moved the same distance during each iteration of the loop, such that this will not always be the case.

The loop continues until the light detector 52 transmits a signal that is not acceptable. It is understood that the position of the light source 50 when the light detector 52 last transmitted an acceptable signal is the position in which the light source 50 was aligned with a second or trailing edge of the first end wall 86 of the prismatic reflector 80 (with the light source 50 being aligned with the first end wall 86 at all positions between the positions in which the light source 50 was aligned with the leading and trailing edges of the first end wall 86). In the illustrated embodiment, in which the light source 50 is moved upwardly from a low extreme position A toward a high extreme position B, the second or trailing edge of the first end wall 86 will be the upper edge of the first end wall 86.

Once the light detector 52 transmits a signal that is not acceptable, the routine will return to the analysis of step 312. At this time, the controller 18 (or some other controller associated with the adjustment system 90) will determine that acceptable signals were previously received from the light detector 52, indicated in FIG. 33 as an arrow from 312 to 320. At step 320, the controller 18 (or some other controller associated with the adjustment system 90) will command the adjustment system 90 to operate in a reverse direction until the light source 50 has been moved into alignment with the midpoint of the first end wall 86 of the prismatic reflector 80. This distance is determined by dividing the distance over which the light detector 52 was transmitting acceptable signals (which is equal to signalSteps in the illustrated embodiment) by two. As noted above, the light detector 52 will transmit acceptable signals between the position at which the light source 50 was aligned with the first or leading edge of the first end wall 86 and the position at which the light source 50 was aligned with the second or trailing edge of the first end wall 86, such that dividing that distance by two will be equal to the distance that the light source 50 must travel in the reverse direction from the trailing edge of the first end wall 86 to arrive at the midpoint of the first end wall 86 (i.e., signalSteps/2 in the illustrated embodiment).

If the expected distance between the leading and trailing edges of the first end wall 86 of the prismatic reflector 80 is known, it is possible to instead determine the position of the midpoint of the first end wall 86 based only on the position of the leading edge of the first end wall 86. In particular, once the position of the leading edge of the first end wall 86 has been identified (i.e., once the first acceptable signal has been transmitted by the light detector 52), the adjustment system 90 may be commanded to move the light source 50 a distance equal to half the (known) distance between the leading and trailing edges of the first end wall 86, thus arriving at the midpoint of the first end wall 86. This approach may be quicker than scanning the entire first end wall 86, but may be less accurate, on account of the actual distance between the leading and trailing edges of the first end wall 86 possibly being slightly different from the expected distance. Thus, when circumstances allow for both of these approaches to be employed, the selection between the two may be based on whether speed or accuracy is prioritized.

With the light source 50 is aligned with the midpoint of the first end wall 86 of the prismatic reflector 80, the controller 18 (or some other controller associated with the adjustment system 90) will determine whether the signal transmitted by the light detector 52 is acceptable, as indicated at 322 in FIG. 33. In the illustrated embodiment, the acceptability of the signal is determined by comparing the measured amplitude to the minimum amplitude or threshold value and comparing the measured pulse width to the target or expected pulse width (as in the analyses performed at 310 and 314, respectively). However, it is within the scope of the present disclosure for some other criteria to be selected to determine whether the signal is acceptable.

If the signal is acceptable, the current position of the light source 50 is deemed to be the monitoring position, and the adjustment system 90 is commanded to stop moving the light source 50. Otherwise, if the signal is not acceptable (which should not be the case), the calibration phase is repeated, as indicated in FIG. 33 by the arrow extending from 322 to 304.

Compared to the algorithm of FIG. 32 (which finds the first acceptable position for the light source 50), the algorithm of FIG. 33 may take more time to identify and move the light source 50 to the monitoring position. However, the final position of the light source 50 resulting from execution of the algorithm of FIG. 33 may tend to result in a stronger signal than the final position resulting from execution of the algorithm of FIG. 32. Thus, the approach of FIG. 33 may be advantageous when the strength of the signal from the light detector 52 (which equates to the alignment of the light source 50 with the first end wall 86 of the prismatic reflector 80) is emphasized over the speed at which the light source 50 is moved into its monitoring position.

Turning now to the routine of FIG. 34, its initial steps are the same as the routines of FIGS. 32 and 33. The centrifugal separation chamber 32 is rotated about the rotational axis 38 (as indicated at 400 in FIG. 34), a target or expected pulse width is calculated using Equation 1 (as indicated at 402 in FIG. 34), and the light source 50 is moved to its home or initial position (as indicated at 404 in FIG. 34). As noted above with regard to the routine of FIG. 32, the adjustment system 90 may instead be commanded to return the light source 50 to its home or initial position at the end of each procedure, rather than during this calibration phase.

As in the routines of FIGS. 32 and 33, with the light source 50 in its initial position, the adjustment system 90 is commanded to move the light source 50 a predetermined distance (as indicated at 406 in FIG. 34) and the signal from the light detector 52 (if any) is analyzed to determine its amplitude and pulse width (as indicated at 408 in FIG. 34). As described above with regard to the routine of FIG. 32, in the illustrated embodiment, the signal from the light detector 52 is not analyzed when the light source 50 is in its initial position because the initial position has been selected so as to place the light source 50 out of alignment with the first end wall 86 of the prismatic reflector 80 (i.e., at a "non-monitoring" position). However, in embodiments in which the initial position is selected such that the light source 50 may be aligned with the first end wall 86 of the prismatic reflector 80 (i.e., in a possible monitoring position), the signal from the light detector 52 when the light source 50 is in its initial position may be analyzed.

As in the routines of FIGS. 32 and 33, the amplitude of the signal is compared to a minimum amplitude or threshold value, as indicated at 410 in FIG. 34. When the amplitude of the signal from the light detector 52 is less than the minimum amplitude or threshold value (which includes situations in which the light detector 52 does not transmit a signal), the controller 18 (or another controller associated with the adjustment system 90) determines whether one or more acceptable signals (as defined in the above discussion of the routine of FIG. 33) have been received from the light detector 52, as indicated at 412 in FIG. 34.

As noted above, when the initial position of the light source 50 is selected as a non-monitoring position (e.g., one of the extreme positions A and B shown in FIG. 27), at least one (and typically more than one) measurement will take place before an acceptable signal has been received. In this case, the adjustment system 90 is commanded to move the light source 50 to another location (indicated in FIG. 34 as an arrow from 412 to 406) that is farther from the initial position than the position of the light source 50 when the previous signal was analyzed. The signal from the light detector 52 (if any) with the light source 50 in the new position is then analyzed to determine its amplitude and pulse width (as at 408), with the amplitude of the new signal being compared to the minimum amplitude or threshold value (as at 410). This process is repeated until the light source 50 is at a position in which the signal from the light detector 52 has an amplitude that is at least equal to the minimum amplitude or threshold value.

When the amplitude of the signal from the light detector 52 is at least equal to the minimum amplitude or threshold value, the pulse width of the signal is compared to the target pulse width, as indicated at 414 in FIG. 34. In the illustrated embodiment, the signal is analyzed using Equation 2 to determine whether its pulse width is sufficiently close or at least substantially equal to the target pulse width. As explained above with regard to the routine of FIG. 32, it should be understood that FIG. 34 illustrates an exemplary approach to comparing a measured pulse width to a target pulse width. In other exemplary approaches, different upper and lower range values may be employed or the measured pulse width may be required to be equal to the target or expected pulse width.

If the measured pulse width satisfies Equation 2, it is considered to be sufficiently close or at least substantially equal to the target pulse width (i.e., the signal is "acceptable" for the analysis carried out in step 412 of FIG. 34) and the characteristics of the signal (e.g., its amplitude, pulse width, and the location of the light source 50 when the signal was transmitted) are saved, as indicated at 416 in FIG. 34. Otherwise, if the measured pulse width does not satisfy Equation 2 (i.e., if the signal is not "acceptable"), the characteristics of the signal are not saved. In either case, the light source 50 is moved again (as at 406), followed by the amplitude and pulse width of the signal from the light detector 52 being analyzed (as at 408, 410, and 414) and the characteristics of the signal (when acceptable) being saved.

The next time that a signal is found in step 408 to have an amplitude that is less than the minimum amplitude or threshold value (which includes failure of the light detector 52 to transmit a signal, on account of the light source 50 being out of alignment with the first end wall 86 of the prismatic reflector 80), the controller 18 (or some other controller associated with the adjustment system 90) again determines whether acceptable signals have been previously received from the light detector 52 (again, as at 412). As acceptable signals have already been received, the controller 18 (or some other controller associated with the adjustment system 90) moves to the final analysis step, which is indicated at 418 in FIG. 34.

In the final analysis step 418, the controller 18 (or some other controller associated with the adjustment system 90) determines the monitoring position of the light source 50. In the illustrated embodiment, this is done by comparing the characteristics of the signals that were saved (at step 416) and selecting the position of the light source 50 at the time that the signal having the greatest amplitude was transmitted by the light detector 52. It will be seen that, during the course of execution of the routine of FIG. 34, the light source 50 will be moved (in one direction) into and then out of alignment with the first end wall 86 of the prismatic reflector 80, such that all of the acceptable positions of the light source 50 are considered during this analysis step 418. The signal having the greatest amplitude corresponds to the position at which the light source 50 is best aligned with the first end wall 86, such that the algorithm of FIG. 34 determines not only an acceptable position for the light source 50, but an optimal position.

It may be the case that multiple signals have the same amplitude, such as when the light detector 52 is saturated. In that case, any one of those signals may be selected to determine the monitoring position for the light source 50. Otherwise, the pulse widths of such signals may be compared, with the pulse widths being used to select the signal that determines the monitoring position for the light source 50. In one embodiment, the signal having the pulse width closest to the calculated target pulse width is selected to determine the monitoring position for the light source 50, while the signal having the greatest pulse width is selected in another embodiment.

In any event, once one of the signals has been selected, the adjustment system 90 is commanded to move the light source 50 to the position that the light source 50 was in at the time that the selected signal was transmitted by the light detector 52. Compared to the algorithms of FIGS. 32 and 33, the algorithm of FIG. 34 may take more time and require more calculations or operations to identify and move the light source 50 to the monitoring position. However, the final position of the light source 50 resulting from execution of the algorithm of FIG. 34 will tend to result in a stronger signal than the final positions resulting from execution of the algorithms of FIGS. 32 and 33. Thus, the approach of FIG. 34 may be advantageous when the strength of the signal from the light detector 52 (and, hence, the alignment of the light source 50 with the first end wall 86 of the prismatic reflector 80) is prioritized.

Again, it should be understood that the illustrated adjustment system 90 and the algorithms of FIGS. 32-34 are merely exemplary and specific to adjustment of the position of the light source 50 of one specifically configured interface monitoring assembly. The principles described herein (which include: providing a movable light source, assessing the strength of the signals transmitted by an associated light detector as the light source is moved, using at least one of the signals as a basis for determining a monitoring position for the light source, and moving the light source to that monitoring position) may be adapted for use with differently configured detection assemblies without departing from the scope of the present disclosure.

ASPECTS

Aspect 1. A fluid processing device, comprising: a detection assembly including a light source associated with a component of the fluid processing device, provided in an initial position with respect to said component of the fluid processing device, and configured to emit a light, an adjustment system associated with the light source and configured to adjust the position of the light source with respect to said component of the fluid processing device, and a light detector configured to receive at least a portion of the light from the light source and generate a signal indicative of the amount of light received by the light detector; and a controller configured to receive the signal from the light detector and control the adjustment system to move the light source with respect to said component of the fluid processing device to a monitoring position based at least in part on the signal.

Aspect 2. The fluid processing device of Aspect 1, wherein the controller is configured to (a) receive and analyze the signal from the light detector, (b) control the adjustment system to move the light source to a different position, and (c) repeat (a) and (b) for a plurality of different positions of the light source before controlling the adjustment system to move the light source to the monitoring position.

Aspect 3. The fluid processing device of Aspect 2, wherein the controller is configured to analyze the signal from the light detector to determine a pulse width and an amplitude of the signal, compare the pulse width of the signal to an expected pulse width and compare the amplitude of the signal to a minimum amplitude for at least one position of the light source, and upon first determining that the pulse width of the signal is either equal to the expected pulse width or at least substantially equal to the expected pulse width and that the amplitude of the signal is at least equal to the minimum amplitude, determine that the current position of the light source is the monitoring position and control the adjustment system to stop moving the light source.

Aspect 4. The fluid processing device of Aspect 2, wherein the controller is configured to (a) analyze the signal from the light detector to determine an amplitude of the signal, (b) upon determining that the amplitude of the signal is at least equal to a minimum amplitude, analyze the signal to determine a pulse width of the signal and compare the pulse width of the signal to an expected pulse width, (c) repeat (a) and (b) for said plurality of different positions of the light source, (d) determine the first position of the light source at which the amplitude of the signal is at least equal to the minimum amplitude and the pulse width of the signal is either equal to the expected pulse width or at least substantially equal to the expected pulse width, (e) determine the last position of the light source at which the amplitude of the signal is at least equal to the minimum amplitude and the pulse width of the signal is either equal to the expected pulse width or at least substantially equal to the expected pulse width, and (f) determine that the monitoring position is midway between said first position and said last position.

Aspect 5. The fluid processing device of Aspect 2, wherein the controller is configured to (a) analyze the signal from the light detector to determine an amplitude of the signal, (b) upon determining that the amplitude of the signal is at least equal to a minimum amplitude, analyze the signal to determine a pulse width of the signal and compare the pulse width of the signal to an expected pulse width, repeat (a) and (b) for said plurality of different positions of the light source, upon determining that there are multiple positions of the light source at which the signal is at least equal to the minimum amplitude and the pulse width of the signal is equal to the expected pulse width or at least substantially equal to the expected pulse width, compare the amplitude of the signal for said multiple positions, and determine that the monitoring position is at one of said multiple positions at which the signal from the light detector has the greatest amplitude.

Aspect 6. The fluid processing device of Aspect 5, wherein the controller is configured to upon determining that the signal from the light detector has the greatest amplitude at at least two positions of the light source, compare the pulse width of the signal for said at least two positions, and determine that the monitoring position is at the position amongst said at least two positions at which the pulse width of the signal is closest to the expected pulse width.

Aspect 7. The fluid processing device of any one of the preceding Aspects, wherein the initial position of the light source is selected to be a non-monitoring position.

Aspect 8. The fluid processing device of any one of the preceding Aspects, further comprising a centrifugal separator configured to rotate about a rotational axis, wherein the adjustment system is configured to move the light source in a direction parallel to the rotational axis.

Aspect 9. The fluid processing device of Aspect 8, wherein the light source is configured to emit the light in a plane orthogonal to the rotational axis, and the light detector is configured to receive said at least a portion of the light in a direction at least generally parallel to the rotational axis.

Aspect 10. The fluid processing device of any one of the preceding Aspects, wherein the light source is associated with a stationary component of the fluid processing device.

Aspect 11. The fluid processing device of any one of the preceding Aspects, wherein the adjustment system includes a carriage receiving at least a portion of the light source, a lead screw associated with the carriage, and a stepper motor configured to be actuated by the controller to rotate the lead screw, thereby moving the carriage and the light source with respect to said component of the fluid processing device.

Aspect 12. The fluid processing device of any one of the preceding Aspects, wherein the adjustment system includes a home sensor configured to determine the initial position of the light source with respect to said component of the fluid processing device.

Aspect 13. A method of adjusting the position of a light source of a detection assembly including a light source and a light detector, the light source being associated with a component of a fluid processing device and provided in an initial position with respect to said component of the fluid processing device, the method comprising: emitting a light from the light source; receiving at least a portion of the light with the light detector and generating a signal indicative of the amount of light received by the light detector; and moving the light source with respect to said component of the fluid processing device to a monitoring position based at least in part on the signal.

Aspect 14. The method of Aspect 13, including (a) receiving and analyzing the signal from the light detector, (b) moving the light source to a different position, and (c) repeating (a) and (b) for a plurality of different positions of the light source before moving the light source to the monitoring position.

Aspect 15. The method of Aspect 14, further comprising analyzing the signal from the light detector to determine a pulse width and an amplitude of the signal, comparing the pulse width of the signal to an expected pulse width and comparing the amplitude of the signal to a minimum amplitude for at least one position of the light source, and upon first determining that the pulse width of the signal is either equal to the expected pulse width or at least substantially equal to the expected pulse width and that the amplitude of the signal is at least equal to the minimum amplitude, determining that the current position of the light source is the monitoring position and stopping movement of the light source.

Aspect 16. The method of Aspect 14, further comprising (a) analyzing the signal from the light detector to determine an amplitude of the signal, (b) upon determining that the amplitude of the signal is at least equal to a minimum amplitude, analyzing the signal to determine a pulse width of the signal and comparing the pulse width of the signal to an expected pulse width, (c) repeating (a) and (b) for said plurality of different positions of the light source, (d) determining the first position of the light source at which the amplitude of the signal is at least equal to the minimum amplitude and the pulse width of the signal is either equal to the expected pulse width or at least substantially equal to the expected pulse width, (e) determining the last position of the light source at which the amplitude of the signal is at least equal to the minimum amplitude and the pulse width of the signal is either equal to the expected pulse width or at least substantially equal to the expected pulse width, and (f) determining that the monitoring position is midway between said first position and said last position.

Aspect 17. The method of Aspect 14, further comprising (a) analyzing the signal from the light detector to determine an amplitude of the signal, (b) upon determining that the amplitude of the signal is at least equal to a minimum amplitude, analyzing the signal to determine a pulse width of the signal and compare the pulse width of the signal to an expected pulse width, repeating (a) and (b) for said plurality of different positions of the light source, upon determining that there are multiple positions of the light source at which the signal is at least equal to the minimum amplitude and the pulse width of the signal is equal to the expected pulse width or at least substantially equal to the expected pulse width, comparing the amplitude of the signal for said multiple positions, and determining that the monitoring position is at one of said multiple positions at which the signal from the light detector has the greatest amplitude.

Aspect 18. The method of Aspect 17, further comprising upon determining that the signal from the light detector has the greatest amplitude at at least two positions of the light source, comparing the pulse width of the signal for said at least two positions, and determining that the monitoring position is at the position amongst said at least two positions at which the pulse width of the signal is closest to the expected pulse width.

Aspect 19. The method of any one of Aspects 13-18, wherein the initial position of the light source is selected to be a non-monitoring position.

Aspect 20. The method of any one of Aspects 13-19, wherein the light source is configured for movement in a direction parallel to a rotational axis of a centrifugal separator.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A fluid processing device, comprising:
a detection assembly including
a light source associated with a component of the fluid processing device, provided in an initial position with respect to said component of the fluid processing device, and configured to emit a light,
an actuator associated with the light source and configured to adjust the position of the light source with respect to said component of the fluid processing device, and
a light detector configured to receive at least a portion of the light from the light source and generate a signal indicative of the amount of light received by the light detector; and
a controller configured to receive the signal from the light detector and control the actuator to move the light source with respect to said component of the fluid processing device to a monitoring position based at least in part on the signal, wherein the initial position of the light source is controlled by the controller in combination with the actuator to be a non-monitoring position in which the light emitted by the light source is not received by the light detector.

2. The fluid processing device of claim 1, further comprising a centrifugal separator configured to rotate about a rotational axis, wherein the actuator is configured to move the light source in a direction parallel to the rotational axis.

3. The fluid processing device of claim 2, wherein
the light source is configured to emit the light in a plane orthogonal to the rotational axis, and
the light detector is configured to receive said at least a portion of the light in a direction at least generally parallel to the rotational axis.

4. The fluid processing device of claim 1, wherein the light source is associated with a stationary component of the fluid processing device.

5. The fluid processing device of claim 1, wherein the actuator includes
a carriage receiving at least a portion of the light source,
a lead screw associated with the carriage, and
a stepper motor configured to be actuated by the controller to rotate the lead screw, thereby moving the carriage and the light source with respect to said component of the fluid processing device.

6. The fluid processing device of claim 1, wherein the actuator includes a home sensor configured to determine the initial position of the light source with respect to said component of the fluid processing device.

7. A fluid processing device, comprising:
a detection assembly including
a light source associated with a component of the fluid processing device, provided in an initial position with respect to said component of the fluid processing device, and configured to emit a light,
an actuator associated with the light source and configured to adjust the position of the light source with respect to said component of the fluid processing device, and
a light detector configured to receive at least a portion of the light from the light source and generate a signal indicative of the amount of light received by the light detector; and
a controller configured to receive the signal from the light detector and control the actuator to move the light source with respect to said component of the fluid processing device to a monitoring position based at least in part on the signal, wherein the controller is further configured to
(a) receive and analyze the signal from the light detector,
(b) control the actuator to move the light source to a different position, and
(c) repeat (a) and (b) for a plurality of different positions of the light source before controlling the actuator to move the light source to the monitoring position.

8. The fluid processing device of claim 7, wherein the controller is configured to
analyze the signal from the light detector to determine a pulse width and an amplitude of the signal,
compare the pulse width of the signal to an expected pulse width and compare the amplitude of the signal to a minimum amplitude for at least one position of the light source, and
upon first determining that the pulse width of the signal is either equal to the expected pulse width or at least substantially equal to the expected pulse width and that the amplitude of the signal is at least equal to the minimum amplitude, determine that the current position of the light source is the monitoring position and control the actuator to stop moving the light source.

9. The fluid processing device of claim 7, wherein the controller is configured to
(a) analyze the signal from the light detector to determine an amplitude of the signal,
(b) upon determining that the amplitude of the signal is at least equal to a minimum amplitude, analyze the signal to determine a pulse width of the signal and compare the pulse width of the signal to an expected pulse width,
(c) repeat (a) and (b) for said plurality of different positions of the light source,
(d) determine a first position of the light source at which the amplitude of the signal is at least equal to the minimum amplitude and the pulse width of the signal is either equal to the expected pulse width or at least substantially equal to the expected pulse width,
(e) determine a last position of the light source at which the amplitude of the signal is at least equal to the minimum amplitude and the pulse width of the signal is either equal to the expected pulse width or at least substantially equal to the expected pulse width, and
(f) control the actuator to move the light source to a location midway between said first position and said last position, with said location serving as the monitoring position.

10. The fluid processing device of claim 7, wherein the controller is configured to
(a) analyze the signal from the light detector to determine an amplitude of the signal,
(b) upon determining that the amplitude of the signal is at least equal to a minimum amplitude, analyze the signal to determine a pulse width of the signal and compare the pulse width of the signal to an expected pulse width,
repeat (a) and (b) for said plurality of different positions of the light source,
upon determining that there are multiple positions of the light source at which the signal is at least equal to the minimum amplitude and the pulse width of the signal is equal to the expected pulse width or at least substantially equal to the expected pulse width, compare the amplitude of the signal for said multiple positions, and determine that the monitoring position is at one of said multiple positions at which the signal from the light detector has the greatest amplitude.

11. The fluid processing device of claim 10, wherein the controller is configured to upon determining that the signal from the light detector has the greatest amplitude at at least two positions of the light source, compare the pulse width of the signal for said at least two positions, and determine that the monitoring position is at the position amongst said at least two positions at which the pulse width of the signal is closest to the expected pulse width.

12. A controller-implemented method of adjusting the position of a light source of a detection assembly including a light source and a light detector, the light source being associated with a component of a fluid processing device and provided in an initial position with respect to said component of the fluid processing device, the method comprising:

emitting a light from the light source;

receiving at least a portion of the light with the light detector and generating a signal indicative of the amount of light received by the light detector; and controlling an actuator to move the light source with respect to said component of the fluid processing device to a monitoring position based at least in part on the signal, wherein the initial position of the light source is controlled by the controller in combination with the actuator to be a non-monitoring position in which the light emitted by the light source is not received by the light detector.

13. The method of claim 12, including (a) receiving and analyzing the signal from the light detector, (b) controlling the actuator to move the light source to a different position, and (c) repeating (a) and (b) for a plurality of different positions of the light source before controlling the actuator to move the light source to the monitoring position.

14. The method of claim 13, further comprising analyzing the signal from the light detector to determine a pulse width and an amplitude of the signal, comparing the pulse width of the signal to an expected pulse width and comparing the amplitude of the signal to a minimum amplitude for at least one position of the light source, and upon first determining that the pulse width of the signal is either equal to the expected pulse width or at least substantially equal to the expected pulse width and that the amplitude of the signal is at least equal to the minimum amplitude, determining that the current position of the light source is the monitoring position and stopping movement of the light source.

15. The method of claim 13, further comprising (a) analyzing the signal from the light detector to determine an amplitude of the signal, (b) upon determining that the amplitude of the signal is at least equal to a minimum amplitude, analyzing the signal to determine a pulse width of the signal and comparing the pulse width of the signal to an expected pulse width, (c) repeating (a) and (b) for said plurality of different positions of the light source, (d) determining the first position of the light source at which the amplitude of the signal is at least equal to the minimum amplitude and the pulse width of the signal is either equal to the expected pulse width or at least substantially equal to the expected pulse width, (e) determining the last position of the light source at which the amplitude of the signal is at least equal to the minimum amplitude and the pulse width of the signal is either equal to the expected pulse width or at least substantially equal to the expected pulse width, and (f) determining that the monitoring position is midway between said first position and said last position.

16. The method of claim 13, further comprising (a) analyzing the signal from the light detector to determine an amplitude of the signal, (b) upon determining that the amplitude of the signal is at least equal to a minimum amplitude, analyzing the signal to determine a pulse width of the signal and compare the pulse width of the signal to an expected pulse width, repeating (a) and (b) for said plurality of different positions of the light source, upon determining that there are multiple positions of the light source at which the signal is at least equal to the minimum amplitude and the pulse width of the signal is equal to the expected pulse width or at least substantially equal to the expected pulse width, comparing the amplitude of the signal for said multiple positions, and determining that the monitoring position is at one of said multiple positions at which the signal from the light detector has the greatest amplitude.

17. The method of claim 16, further comprising upon determining that the signal from the light detector has the greatest amplitude at at least two positions of the light source, comparing the pulse width of the signal for said at least two positions, and determining that the monitoring position is at the position amongst said at least two positions at which the pulse width of the signal is closest to the expected pulse width.

18. The method of claim 12, wherein the light source is configured for movement in a direction parallel to a rotational axis of a centrifugal separator.

* * * * *